(12) United States Patent
Dunne

(10) Patent No.: US 9,550,025 B2
(45) Date of Patent: Jan. 24, 2017

(54) INJECTOR

(75) Inventor: Stephen Terence Dunne, Ipswich (GB)

(73) Assignee: NEW INJECTION SYSTEMS LTD., Stowmarket (GB)

( * ) Notice: Subject to any disclaimer, the term of this patent is extended or adjusted under 35 U.S.C. 154(b) by 578 days.

(21) Appl. No.: 13/637,053

(22) PCT Filed: Mar. 25, 2011

(86) PCT No.: PCT/GB2011/000437
§ 371 (c)(1),
(2), (4) Date: Jun. 24, 2014

(87) PCT Pub. No.: WO2011/117592
PCT Pub. Date: Sep. 29, 2011

(65) Prior Publication Data
US 2013/0197475 A1    Aug. 1, 2013

(30) Foreign Application Priority Data

Mar. 25, 2010 (GB) .................................. 1005014.4
Apr. 23, 2010 (GB) .................................. 1006781.7

(Continued)

(51) Int. Cl.
*A61M 5/178* (2006.01)
*A61M 5/20* (2006.01)
(Continued)

(52) U.S. Cl.
CPC ......... *A61M 5/2053* (2013.01); *A61M 5/2033* (2013.01); *A61M 5/2425* (2013.01);
(Continued)

(58) Field of Classification Search
CPC .. A61M 5/326; A61M 2005/206; A61M 5/20; A61M 5/46; A61M 2005/2013; A61M 2005/3128
See application file for complete search history.

(56) References Cited

U.S. PATENT DOCUMENTS 906,574 A    12/1908  Stebbins
2,871,856 A   2/1959  Steiner
(Continued)

FOREIGN PATENT DOCUMENTS

DE    19622124 A1   12/1997
EP     0361668 B1    7/1994
(Continued)

OTHER PUBLICATIONS

PCT International Search Report and Written Opinion dated Apr. 7, 2011 for PCT/GB2011/000437 from which the instant application is based.
(Continued)

*Primary Examiner* — Emily Schmidt
(74) *Attorney, Agent, or Firm* — Fredrikson & Byron, P.A.

(57) ABSTRACT

An injector for delivering medicament comprises a collapsible container (1002) for containing the liquid medicament, a normally-closed valve (1004) coupled to the collapsible container (1002) for retaining the liquid medicament within the collapsible container and an injection means (1006) for delivering the liquid medicament from the collapsible container. The liquid medicament is maintained under pressure by a pressurizing means (1003) which pressurizes the liquid medicament such that it is delivered by the injection means (1006) when the normally-closed valve (1004) is opened.

45 Claims, 28 Drawing Sheets

(30) Foreign Application Priority Data

Figure 1:
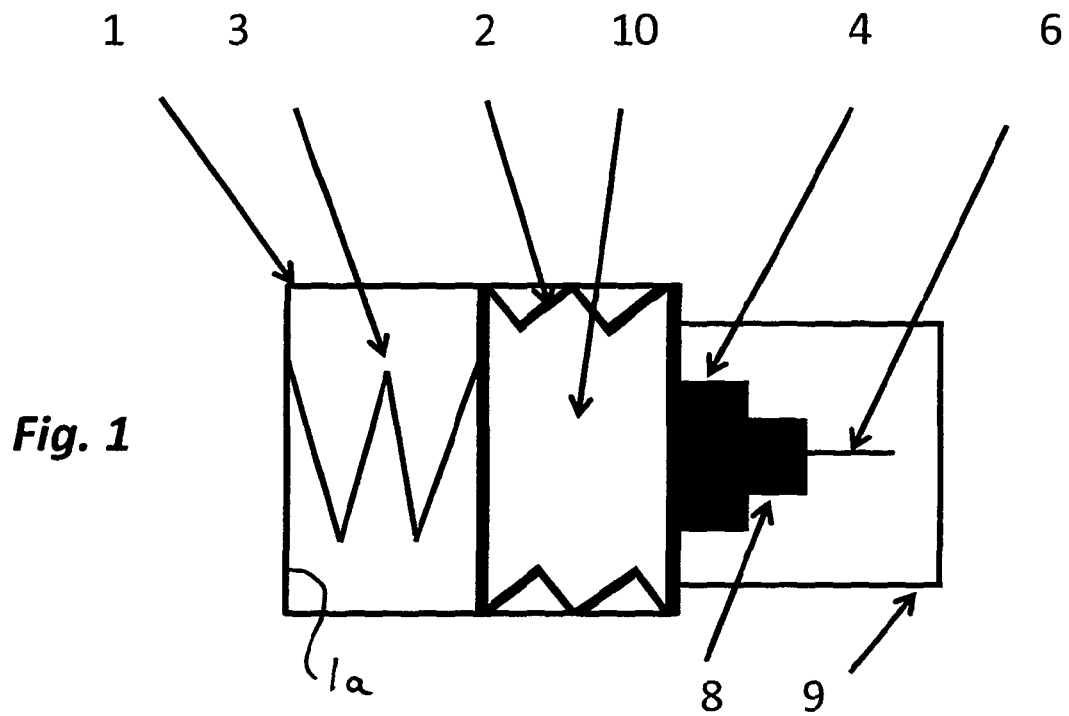

| | | |
|---|---|---|
| May 20, 2010 | (GB) | 1008406.9 |
| May 25, 2010 | (GB) | 1008640.3 |
| Jun. 14, 2010 | (GB) | 1009896.0 |
| Jun. 15, 2010 | (GB) | 1009954.7 |
| Jun. 22, 2010 | (GB) | 1010403.2 |
| Aug. 17, 2010 | (GB) | 1013738.8 |

(51) Int. Cl.
- A61M 5/24 (2006.01)
- A61M 5/32 (2006.01)
- A61M 5/50 (2006.01)
- A61M 5/31 (2006.01)

(52) U.S. Cl.
CPC ............ A61M 5/326 (2013.01); A61M 5/3216 (2013.01); A61M 5/3243 (2013.01); A61M 5/5086 (2013.01); A61M 2005/2013 (2013.01); A61M 2005/3128 (2013.01); A61M 2005/3247 (2013.01)

(56) References Cited

U.S. PATENT DOCUMENTS

| | | | |
|---|---|---|---|
| 3,207,157 A | | 9/1965 | Murdoch |
| 3,403,679 A | | 10/1968 | Sinclair |
| 4,093,108 A | * | 6/1978 | Hein ............... A61M 5/31511 222/401 |
| 4,265,241 A | * | 5/1981 | Portner ............ A61M 5/14276 128/DIG. 12 |
| 4,997,420 A | * | 3/1991 | LeFevre ............ A61M 5/145 128/DIG. 12 |
| 5,100,389 A | * | 3/1992 | Vaillancourt ...... A61M 5/1454 604/135 |
| 5,271,527 A | * | 12/1993 | Haber ............. A61M 5/19 222/137 |
| 5,346,476 A | * | 9/1994 | Elson ............. A61M 5/148 604/135 |
| 5,626,567 A | * | 5/1997 | Gmeiner ................. 604/236 |
| 6,183,440 B1 | | 2/2001 | Bell |
| 6,277,099 B1 | | 8/2001 | Strowe et al. |
| 6,443,152 B1 | | 9/2002 | Lockhart et al. |
| 6,585,698 B1 | | 7/2003 | Packman et al. |
| 6,605,058 B1 | | 8/2003 | Wich |
| 6,641,561 B1 | | 11/2003 | Hill et al. |
| 6,648,859 B2 | | 11/2003 | Bitdinger et al. |
| 6,689,101 B2 | | 2/2004 | Hjertman et al. |
| 6,755,810 B1 | | 6/2004 | Buch-Rasmussen et al. |
| 6,979,316 B1 | | 12/2005 | Rubin et al. |
| 6,981,963 B2 | | 1/2006 | Barker et al. |
| 7,338,469 B2 | | 3/2008 | Barker et al. |
| 7,402,150 B2 | | 7/2008 | Matsumoto et al. |
| 7,708,719 B2 | | 5/2010 | Wilmot et al. |
| 7,717,877 B2 | | 5/2010 | Lavi et al. |
| 7,736,333 B2 | | 6/2010 | Gillespie, III |
| 7,927,303 B2 | | 4/2011 | Wyrick |
| 7,955,304 B2 | | 6/2011 | Guillermo |
| 7,976,514 B2 | | 7/2011 | Abry et al. |
| 8,038,649 B2 | | 10/2011 | Kronestedt |
| 8,062,255 B2 | | 11/2011 | Brunnberg et al. |
| 8,123,724 B2 | | 2/2012 | Gillespie, III |
| 8,162,917 B2 | | 4/2012 | Stepovich et al. |
| 8,235,952 B2 | | 8/2012 | Wikner |
| 8,251,947 B2 | | 8/2012 | KraMer et al. |
| 8,308,695 B2 | | 11/2012 | Laiosa |
| 8,328,753 B2 | | 12/2012 | Solomon et al. |
| 8,361,025 B2 | | 1/2013 | Lawlis et al. |
| 8,523,807 B2 | | 9/2013 | Reynolds et al. |
| 8,597,257 B2 | | 12/2013 | Modi |
| 8,651,334 B2 | | 2/2014 | Suchan et al. |
| 8,672,901 B2 | | 3/2014 | Bollenbach et al. |
| 8,721,602 B2 | | 5/2014 | Poveda Estepa |
| 8,753,319 B2 | | 6/2014 | Davies et al. |
| 2001/0056259 A1 | | 12/2001 | Skinkle |
| 2003/0106824 A1 | * | 6/2003 | Wilmot et al. ............... 206/439 |
| 2003/0216683 A1 | * | 11/2003 | Shekalim ............ A61M 5/1454 604/67 |
| 2006/0275336 A1 | * | 12/2006 | Du Plessis ................ 424/423 |
| 2008/0039789 A1 | * | 2/2008 | Wyrick ................ 604/110 |
| 2008/0058732 A1 | | 3/2008 | Harris |
| 2008/0097308 A1 | * | 4/2008 | Schiller et al. ............ 604/110 |
| 2009/0024083 A1 | * | 1/2009 | Kriesel ............ A61M 5/14244 604/86 |
| 2009/0112163 A1 | | 4/2009 | Bivin et al. |
| 2009/0198185 A1 | * | 8/2009 | Gonnelli ............ A61M 5/1452 604/151 |
| 2010/0036319 A1 | | 2/2010 | Drake et al. |
| 2010/0114059 A1 | * | 5/2010 | Hiniduma-Lokuge A61M 5/1452 604/500 |
| 2010/0137832 A1 | | 6/2010 | Matthews et al. |
| 2010/0191217 A1 | * | 7/2010 | Hommann et al. ............ 604/506 |
| 2010/0280460 A1 | | 11/2010 | Markussen |
| 2011/0213314 A1 | | 9/2011 | Guillermo |
| 2011/0218500 A1 | | 9/2011 | Grunhut et al. |
| 2011/0270220 A1 | | 11/2011 | Genosar |
| 2011/0282298 A1 | | 11/2011 | Agian et al. |
| 2012/0101475 A1 | | 4/2012 | Wilmot et al. |
| 2012/0123346 A1 | | 5/2012 | Davies et al. |
| 2012/0123387 A1 | | 5/2012 | Gonzalez et al. |
| 2012/0130318 A1 | | 5/2012 | Young |
| 2012/0226238 A1 | | 9/2012 | Davies et al. |
| 2013/0041321 A1 | | 2/2013 | Cross |
| 2013/0184677 A1 | | 7/2013 | Py |
| 2013/0197447 A1 | | 8/2013 | Smith |
| 2013/0197474 A1 | | 8/2013 | Bilton et al. |
| 2013/0211330 A1 | | 8/2013 | Pedersen et al. |
| 2013/0218089 A1 | | 8/2013 | Davies et al. |
| 2013/0218093 A1 | | 8/2013 | Markussen et al. |
| 2013/0226080 A1 | | 8/2013 | Davies et al. |
| 2013/0226081 A1 | | 8/2013 | Davies et al. |
| 2013/0226096 A1 | | 8/2013 | Jugl |
| 2013/0296807 A1 | | 11/2013 | Lintern et al. |
| 2013/0296824 A1 | | 11/2013 | Mo et al. |
| 2014/0025014 A1 | | 1/2014 | Radmer et al. |
| 2014/0025015 A1 | | 1/2014 | Cross et al. |
| 2014/0031760 A1 | | 1/2014 | Mercer et al. |
| 2014/0066861 A1 | | 3/2014 | Auernhammer |
| 2014/0081239 A1 | | 3/2014 | Cronenberg |
| 2014/0088512 A1 | | 3/2014 | Quinn |
| 2014/0094757 A1 | | 4/2014 | Mercer et al. |

FOREIGN PATENT DOCUMENTS

| | | | |
|---|---|---|---|
| EP | 0879611 A3 | 2/1999 | |
| EP | 0906131 B1 | 1/2003 | |
| EP | 0996476 B1 | 5/2003 | |
| EP | 1024845 B1 | 7/2003 | |
| EP | 1698364 B1 | 7/2008 | |
| EP | 1927372 B1 | 6/2009 | |
| EP | 0609741 A1 | 12/2010 | |
| EP | 2258426 A1 | 12/2010 | |
| EP | 2436411 A1 | 4/2012 | |
| EP | 2605814 A2 | 6/2013 | |
| EP | 2704772 A1 | 3/2014 | |
| FR | 1143900 A | 10/1957 | |
| GB | 0906574 A | 9/1962 | |
| JP | WO 2009119496 A1 | * 10/2009 | ............ A61M 5/28 |
| WO | WO 9632344 A1 | 10/1996 | |
| WO | 9842394 A1 | 10/1998 | |
| WO | 9916485 A1 | 4/1999 | |
| WO | 0028941 A2 | 5/2000 | |
| WO | WO 2005075105 A1 | 8/2005 | |
| WO | 2006057636 A1 | 6/2006 | |
| WO | WO 2007034226 A1 | 3/2007 | |
| WO | WO 2010022870 A1 | 3/2010 | |
| WO | WO 2011117592 A1 | 9/2011 | |
| WO | 2012013585 A1 | 2/2012 | |
| WO | 2012058192 A1 | 5/2012 | |
| WO | 2013079652 A2 | 6/2013 | |
| WO | 2013124139 A1 | 8/2013 | |
| WO | 2014001319 A1 | 1/2014 | |

(56) References Cited

FOREIGN PATENT DOCUMENTS

| WO | 2014060563 A2 | 4/2014 |
| WO | 2014080020 A1 | 5/2014 |
| WO | WO 2014076282 A1 | 5/2014 |
| WO | WO 2015121655 A1 | 8/2015 |

OTHER PUBLICATIONS

PCT International Search Report and Written Opinion dated Feb. 26, 2014 for PCT/EP2013/074084 filed Nov. 18, 2013, 10pgs.
PCT International Search Report and Written Opinion dated Mar. 4, 2014 for PCT/EP2013/074647 filed Nov. 25, 2013, 8 pgs.
Parisien, P. "A Practical Guide for the selection and use of prefilled Syringes for flushing vascular access devices," MEdXI Inc., Montreal, Canada, believed to be available more than one year before the filing date of the priority application in the instant case (Mar. 25, 2010).

* cited by examiner

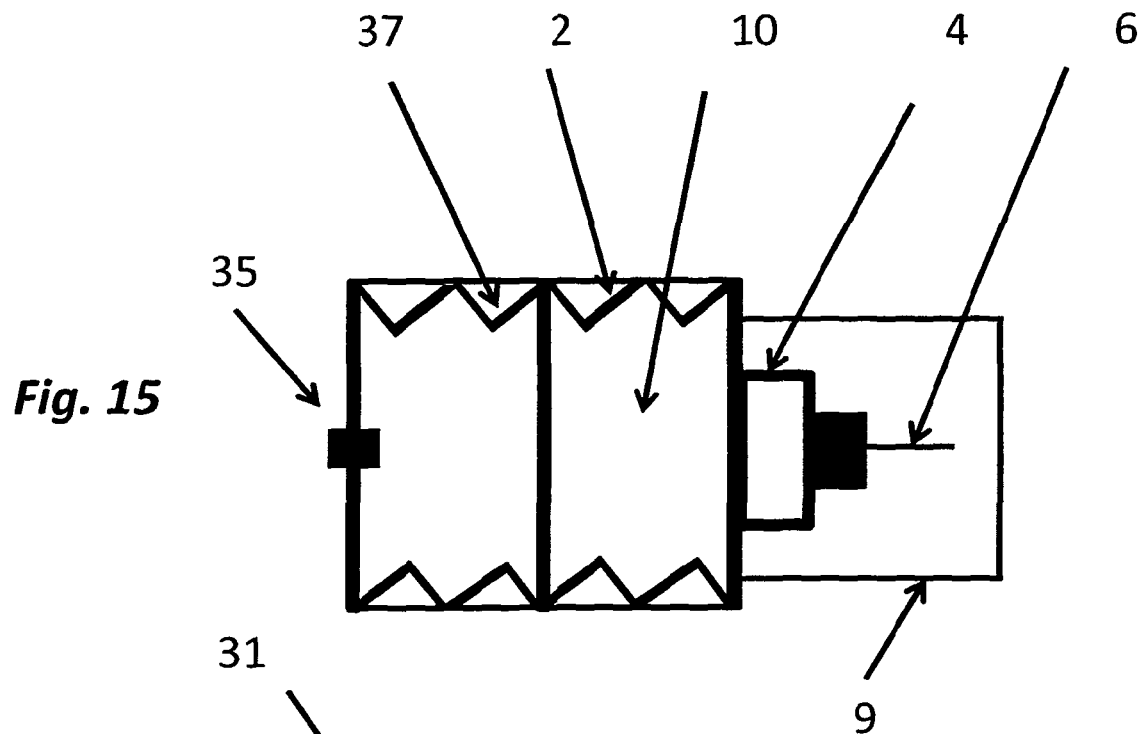
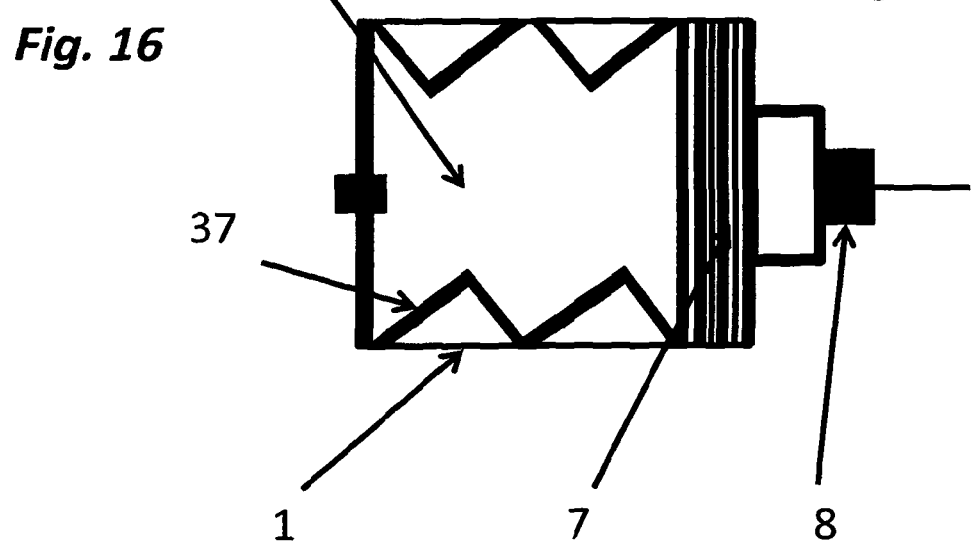

INJECTOR

RELATED APPLICATIONS

This application is a 35 U.S.C. 371 national stage filing from International Application No. PCT/GB2011/00043 filed Mar. 25, 2011 and claims priority to GB Application No. 1005014.4 filed Mar. 25, 2010, GB Application No. 1006781.7 filed Apr. 23, 2010, GB Application No. 1008406.9 filed May 20, 2010, GB Application No. 1008640.3 filed May 25, 2010, GB Application No. 1009896.0 filed Jun. 14, 2010, GB Application No. 1009954.7 filed Jun. 15, 2010, GB Application No. 1010403.2 filed Jun. 22, 2010, and GB Application No. 1013738.8 filed Aug. 17, 2010, the teachings of which are incorporated herein by reference.

The invention relates to an injector for delivering a liquid, for example for delivering a liquid medicament to a human or animal patient. The invention may also relate to a method of injecting a liquid and a method of manufacturing an injector.

BACKGROUND

Pre-filled syringes and auto-injectors are devices that are well known in the prior art for the delivery of liquids, often for the delivery of a liquid medicament to a patient. Both pre-filled syringes and auto-injectors tend to be constructed from a cylindrical barrel for containing the liquid with a plunger and needle to effect delivery of the liquid. The liquid is stored in the barrel and sealed at one end by the plunger and at the other by a cap. Sometimes such devices include a staked needle (i.e. a permanently fixed needle) which will have a cap over the needle to seal the device. The plunger is either depressed by the user to expel the liquid drug via the needle, or, in the case of auto-injectors, the plunger is depressed by an energy source which is often a compression spring.

These conventional devices suffer from many drawbacks including stability problems arising from the interaction of the medicament with the materials forming the device, such as the barrel glass, the plastic elastomeric plunger, the metallic needle, the adhesive used to stake the needle, and any necessary lubricants. The filling of these conventional devices is also problematic. The placement of a plunger during filling makes it difficult to fill many known devices bubble free and without risk of contamination. Movement of a plunger during storage due to expansion and contraction of air bubbles within the filled device may result in contamination of the drug.

Additionally the liquid medicament is sealed within the barrel by a moving plunger. It is, therefore, difficult to completely seal the medicament and keep it sterile while also allowing the plunger to be capable of movement.

Furthermore, the barrel is often made of brittle glass which is breakable both in use and during production and filling.

In most devices the liquid is in contact with the needle during storage. This can lead to problems such as blockages due to drug crystallization within the needle and medicament instability due to the interaction of the drug with the metals in the needle.

The filling procedures for conventional pre-filled syringes need to be complex to ensure sterility at all times.

It is an aim of the invention to provide a better injector.

SUMMARY OF INVENTION

The invention provides an injector, a method of injecting a liquid, and a method of manufacturing an injector as defined in the appended independent claims, to which reference should now be made. Preferred and/or advantageous features of the invention are defined in various dependent sub-claims.

Thus, the invention may provide an injector for delivering a liquid, preferably in which the liquid is a liquid medicament. The injector comprises a collapsible container for containing the liquid, a normally-closed valve coupled to the collapsible container for retaining the liquid within the collapsible container, an injection means coupled to the normally-closed valve for delivering the liquid from the collapsible container, and pressurising means for pressurising the liquid contained within the collapsible container, such that the liquid is delivered by the injection means when the normally-closed valve is opened.

The liquid is preferably a liquid medicament, for example a drug solution or suspension, or a mixture of more than one solution or suspension, for treatment of a disease or condition of a human or animal. It is envisaged, however, that the liquid may not be a medicament, but may be some other injectable liquid. For example, it is known to inject various polymer solutions such as hydrogels into the human or animal body.

It is envisaged that the injection means will preferably be a needle for injection of the liquid, for example a hollow needle such as a hypodermic needle for piercing the skin of a human or animal patient and injecting the liquid into the human or animal body. The injection means may, thus, be a hypodermic needle or some other piercing element such as a micro-needle or a nozzle. The injection means may be an array of needles for piercing the skin. Suitable hypodermic needles may have any standard gauge, for example any needle between G20 and G30. Needles suitable for use with the injector may be micro-needles under 2 mm long, for example, under 1 mm long, or between 0.1 mm and 1 mm long.

The injection means may, alternatively, be a needleless injection element such as are known in the prior art for injecting a liquid into the human or animal body.

The injector may be used to inject the liquid into any part of the human or animal body. The injector may be used to provide intramuscular, subcutaneous, intradermal, or intravenous injections. The device may be used for injecting into other locations, for example for delivering liquid medicaments or other substances into a body's organs or bones.

In preferred embodiments of an injector, the collapsible container and the pressuring means are both housed within a rigid container or body, the rigid container or body forming a component element of the injector. Preferably, the normally-closed valve is connected to the rigid container.

The rigid container may be formed from any suitable material, for example a rigid plastic or metal or glass. Particularly preferred materials may include polyethylene, polypropylene, PET, COC, COP, and Ethylene vinyl alcohol.

The rigid container may be hermetically sealed, such that the contents of the rigid container are shielded from the external environment. Alternatively, the rigid container may be a frame or cage that acts to locate the collapsible container and the pressurising means. It is particularly advantageous if the rigid container is formed from a transparent material, such as a transparent polymer or glass, such that the contents can be viewed and monitored.

The rigid container may comprise a vent to allow displaced air within the rigid container to escape during filling of the collapsible container. Advantageously, the vent may be a closable vent so that the internal contents of the container may be re-sealed after venting. If the rigid container is not entirely made of a transparent material, it may be advantageous that the rigid container includes an observation window for allowing inspection of the rigid container's contents. Such a window may be formed from a transparent material such as glass or plastic, or may simply be a hole in walls of the rigid container where the rigid container is not sealed. Advantageously, the window may be formed as a lens, or incorporating a lens, to facilitate inspection of the liquid contents of the collapsible container.

The liquid being delivered by the injector may be a liquid that is adversely affected by interaction with oxygen. For example, many liquid medicaments react adversely with oxygen and, therefore, have a limited shelf life. Thus, it may be advantageous that the rigid container can be fully sealed from the external environment. In this way, a liquid medicament contained within the collapsible container is less likely to be exposed to the external environment and may have a longer shelf life. Thus, it is preferred that the rigid container is fully seated or, where the container has a vent, that the vent may be plugged. It may be particularly advantageous that the rigid container may be hermetically sealed, preferably with an inert gas atmosphere surrounding the collapsible container. For example, air within the rigid container may be purged by an inert gas that has a low solubility in the liquid medicament, for example nitrogen.

An inert gas atmosphere within the rigid container may be developed during manufacture of the injector. For example, air may be replaced by nitrogen, or any other suitable gas, during valve placement or valve crimping procedures. This may be effected using known under the cup filling procedures. Alternatively, a vacuum may be created during crimping so that, when the collapsible container has been filled with liquid, the atmospheric pressure surrounding the container is close to atmospheric pressure.

Preferably, the collapsible container is a separate sealed container that may expand or collapse to vary the volume within the container. A particularly preferred configuration of the collapsible container is in the form of a bellows. A bellows container has pleated or corrugated sides that allow the container to expand or contract. The collapsible bag or bellows may be made of any material suitable for containing the liquid. For example, where the liquid is a medicament the bag or bellows is preferably any suitable material approved for pharmaceutical use. The bag or bellows may be laminated in order to provide specified material properties. For example, an internal surface of the bag or bellows may be formed from a material having a low reactivity with the liquid, whereas an outer layer or outer layers of the bag may be formed from a material having low liquid transfer properties or low gas transfer properties. The bag may advantageously be formed from or comprise a substantially inert polymeric material such as polyethylene or polypropylene.

It may be particularly advantageous if the collapsible bag or bellows is formed from a transparent material. This allows the contents of the bag or bellows to be inspected visually.

It is preferred that the collapsible container is a bellows that is directly coupled to the normally-closed valve. This configuration allows the bellows to be filled directly through the normally-closed valve, thereby expanding the bellows, and the liquid will be retained within the bellows when the normally-closed valve is closed.

Where the injector comprises a rigid container or body, the collapsible container may be defined within the rigid container. For example, the collapsible container may be defined in part by internal walls of the rigid container and in part by a piston that is slideably arranged within the rigid container, such that the volume of the collapsible container varies depending on the position of the piston. In this arrangement the collapsible container is similar to that defined within a standard syringe. In this example, force from the pressurising means may act via the piston to pressurise the liquid contained within the collapsible container. Where the collapsible container is defined by internal walls of the rigid container and a piston, the normally-closed valve will be coupled to the rigid container, such that the liquid may be delivered through the valve when the normally-closed valve is open. The piston in such a piston/cylinder arrangement may be made of plastic or any other suitable material with or without an elastomer seal.

The pressurising means applies a continuous pressure to the liquid once the collapsible container has been filled. Thus, the liquid is maintained under pressure during storage before use. Preferably, the pressurising means for pressurising the liquid contained within the collapsible container is a biasing element that exerts a force that acts upon the collapsible container, and thereby upon the liquid contained within the collapsible container. Preferably, the force acting to collapse the collapsible container is generated by a resilient means such as a spring, for example a compressed helical spring arranged to urge the collapsible container to collapse.

Where the collapsible container is in the form of a collapsible bag or bellows, the pressurising means may advantageously comprise a spring that forms an integral part of the collapsible container. For example, walls of the collapsible container may be connected to or coupled to a spring that acts to collapse the collapsible container thereby minimising the internal volume of the collapsible container. On filling with the liquid, the spring will be extended and the volume of the collapsible container increased to accommodate the liquid. As the spring is constantly urging towards its un-extended state it pressurises the liquid medicament contained within the collapsible container. While the normally-closed valve is closed, the liquid remains within the collapsible container. When the normally-closed valve is opened, however, the pressure exerted by the integral spring urges the liquid out of the collapsible container through the normally-closed valve.

The force that acts to collapse the collapsible container may be a force generated by a compressed gas or a liquefied gas. For example, the device may comprise a second collapsible container containing a gas that is compressed when the collapsible container is filled with liquid and exerts a force on the collapsible container. Alternatively, where the collapsible container is defined within walls of a rigid container, the force may be generated by a compressed gas acting on a plunger that pressurises the liquid within the collapsible container.

It may be preferable that the injector comprises a rigid container within which the collapsible container and the pressurising means are housed. The pressurising means may then apply a force to the collapsible container and the rigid container simultaneously. As the rigid container is unable to move, the collapsible container is therefore urged into a collapsed state. Thus, the injector may comprise a rigid container housing a collapsible container coupled to a normally-closed valve that extends through a wall of the rigid container, the rigid container further comprising or housing a pressurising means that acts to urge the collapsible container away from an internal surface of the rigid container. The pressuring means may therefore be a resilient spring housed within the rigid container, such that it is compressed when the collapsible container is filled with liquid and acts to collapse the collapsible container when the normally-closed valve is opened. The pressurising means may, alternatively, comprise a compressed gas confined within a second collapsible container that when compressed generates a force that acts on the collapsible container to expel liquid from the collapsible container when the normally-closed valve is opened.

Advantageously, the pressurising means may comprise a piston or ram that is urged into contact with the collapsible container. The piston or ram may be urged by the force of a biasing means such as a helical spring, or other form of spring, or may be forced into contact with the collapsible container by means of a compressed gas or a liquefied gas. Advantageously, the piston or ram may be shaped to reduce or eliminate dead volume in the collapsible container when it is collapsed. For example, the piston or ram may comprise a shaped front portion for contacting the collapsible container, and this shaped front portion may be any suitable shape, for example a substantially conical shape. The shaped piston or ram may force the collapsible container into a shaped portion of the injector, for example a shaped portion of the rigid container, or a shaped entranceway to the normally-closed valve, such that the majority of the contents of the collapsible chamber may be expelled through the normally-closed valve.

The normally-closed valve is an openable valve that may be opened to deliver the liquid or to allow the collapsible container to be filled with the liquid, but is normally closed to retain the liquid in a sealed condition within the collapsible container. Preferably the normally-closed valve is a continuous flow valve or an aerosol valve. The aerosol valve may be a conventional type male aerosol valve or a female aerosol valve, although any normally-closed valve may be used. A conventional aerosol valve with an axial movement opening may be used, or alternatively a toggle action aerosol valve may be used, in which the valve is opened by tilting the valve stem.

Particularly preferably, the normally-closed valve comprises a spring that acts to urge the valve into its closed position. Preferably this spring is a non-metallic spring, for example a plastic spring. An aerosol valve having such a plastic spring is described, for example in U.S. Pat. No. 4,471,893. By using a normally-closed valve comprising a non-metallic spring, the liquid contents of the collapsible container do not contact any metallic surface when the injector is in storage. The stability of the drug within the injector may thus be improved during storage, and safe storage times may be longer than they would otherwise be. It is particularly preferred that the normally-closed valve has a minimised dead space to maximise the percentage of the liquid contents of the collapsible container that may be delivered.

The injector may comprise a manually operated switch for opening the normally-closed valve. For example, the injector may comprise a button or toggle or switch that a user can actuate once the injector is in a predetermined position for injection. The manually operated switch opens the normally-closed valve, thereby allowing the contents of the collapsible container to be delivered or dispensed.

Preferably, the injector comprises an actuator for opening the normally-closed valve automatically when a predetermined condition is met. For example, the injector may comprise an actuator that opens the normally-closed valve when the injector is pressed against a patient's skin.

Conventional autoinjectors deliver their full dose of drug solution after the delivery has been actuated. The use of a normally-closed valve to control delivery of the liquid in injectors according to the invention allows the delivery of the drug to be stopped by closing the valve during delivery, should this be required. This may be particularly advantageous in embodiments of the injector that are manually-actuated. This may allow an injection to be halted if a problem occurs, or allow a break in the injection cycle. This flexibility is currently only provided by standard manual injections.

An injector according to an embodiment of the invention may comprise a collapsible container containing a liquid, a normally-closed valve, a rigid container, means of pressurising the contents of the collapsible bag, and means of piercing skin to enable injection of the liquid.

In a preferred configuration, the injector may comprise a needle injection means for delivering the liquid into the body of a patient, and the normally-closed valve is arranged to actuate when the needle has been inserted a predetermined distance into the patient. This predetermined distance will depend upon the type of drug or medicament that is being delivered to the patient, and the tissue type that the delivery is required to be made into. For example, the injector may be configured to automatically open the normally-closed valve when the needle reaches a predetermined depth into the patient's body.

The switch or actuator for opening the normally-closed valve may include means for gaining a mechanical advantage, such as a lever. This arrangement may be advantageous where the force keeping the normally-closed valve closed is a high one.

It is particularly preferred that the injection means comprises a protective sleeve or shield. This is of greatest advantage where the injector means is a needle, and the protective sleeve or shield thereby provides a safety mechanism to help prevent inadvertent needle stick by the user of the injector. A protective sleeve or shield may also help maintain sterility of the injection means during storage. A passive needle shield is described by US 2009/0227956 or U.S. Pat. No. 5,092,851. A manually activated needle shield may be used, for example, of the type described in U.S. Pat. No. 4,738,663 or U.S. Pat. No. 4,944,397.

It is preferred that the injection means is coupled to the injector during storage, so that a user of the injector has a minimal number of preparation steps to go through before the injector is ready to use. It is possible, however, that the injection means will be supplied separately from the rest of the injector components and will need to be coupled to the normally-closed valve by an operator prior to use.

A particularly advantageous property of the injector is that, as the liquid within the collapsible container is under constant pressure, any leak of liquid from the collapsible container will result in the collapsible container moving. For example, if a collapsible bellows is used, any leak will result in the partial collapse of the bellows as the bellows are under a constant pressure. If the injector has a configuration such that the bellows can be viewed during use, then any collapse of the bellows prior to use can be noted. Thus, it is preferred that the injector comprises a level indicator that shows a user when liquid has escaped from the collapsible container. A level indicator or level indicator marks on the injector may also be useful in order to determine the extent to which the liquid has been delivered from the injector during use.

A further advantage of the injector is that the pressurised system makes it harder for foreign matter or material to contaminate the liquid contents.

In a particularly preferred embodiment, an injector for delivering a liquid medicament comprises a collapsible bellows for containing the liquid medicament, an aerosol valve coupled to the collapsible bellows for retaining the liquid medicament within the collapsible bellows, a hypodermic needle coupled to the aerosol valve for delivering the liquid medicament from the collapsible bellows, a rigid container housing the collapsible bellows and coupled to the normally-closed valve, such that the collapsible bellows are housed within the rigid container and the normally-closed valve allows communication with the collapsible bellows through the walls of the rigid container, and a spring housed within the rigid container acting to urge the collapsible bellows to a collapsed state, thereby pressuring liquid medicament contained within the collapsible bellows such that the liquid medicament is delivered through the hypodermic needle when the aerosol valve is opened.

Particularly preferably, such an injector comprises a piston or ram disposed between the spring and the collapsible bellows, in which the spring urges the piston or ram into contact with the collapsible bellows, thereby pressuring the liquid medicament. Such a piston or ram may act to guide the force applied by the spring and stabilise the engagement between the spring and the collapsible container.

In an alternative aspect, an injector may comprise a liquid medicament retained within a collapsible container by a normally-closed valve, and a needle for injecting the liquid medicament coupled to the normally-closed valve, in which a force is arranged to act on the collapsible container, such that the liquid medicament is delivered through the needle when the normally-closed valve is opened.

Preferably, at least an inner surface of the collapsible container is formed from a polymer, and the normally-closed valve is formed from a polymer, such that the liquid medicament does not come into contact with any metallic component while retained within the collapsible container. Advantageously, the liquid medicament does not contact the needle until the normally-closed valve is opened to deliver the liquid medicament. Preferably, the injector is an injector according to any injector described above, in which the dead volume of the collapsible container and the normally-closed valve are low enough to ensure that more than 85% of the liquid medicament contained within the collapsible container can be delivered. Many medicaments and drugs are expensive and it is desirable to reduce waste as much as possible. Particularly preferably, the injector is configured such that more than 90% or more than 95%, and particularly preferably, more than 97% of the liquid medicament contained within the collapsible container may be delivered.

Advantageously, the injector may be a hand-held injector. A healthcare professional may, therefore, be able to carry a number of injectors each pre-loaded with a liquid medicament that are substantially ready for employment in delivering the liquid medicament. The injector may have improved sterility and stability of drug contents and may allow a dose of drug to be delivered simply and effectively.

Particularly preferably, the injector according to any embodiment described above is filled with the liquid medicament. The liquid medicament may comprise a constituent classified within any one of the following categories of pharmaceuticals or biopharmaceuticals; Alpha1-Adrenergic Antagonists, Analgesic Agents, Anaesthetics, Angiotensin Antagonists, Anti-Inflammatory Agents, Antianxiety Agents, Antiarrhythmics, Anticholinergics, Anticoagulants, Anticonvulsants, Antidiarrheal Agents, Antihistamines, Antineoplastics and Antimetabolites, Antineoplastics and Antimetabolites, Antiplasticity Agents, Antiulcer Agents, Beta-Adrenergic Antagonists, Bisphosphonates, Bronchodilators, Cardiac Inotropes, Cardiovascular Agents, Central Acting Alpha2-stimulants, Contrast Agents, Converting Enzyme Inhibitors, Dermatologics, Diuretics, Drugs for Erectile Dysfunction, Drugs of Abuse, Endothelin Antegonists, Hormonal Agents and Cytokines, Hypoglycemic Agents, Hypouricemic Agents and Drugs Used For Gout, Immunosuppressants, Lipid Lowering Agents, Miscellaneous, Psychotherapeutic Agents, Renin Inhibitors, Serotonergic Antagonist, Steroids, Sympathomimetics, Thyroid and Antithyroid Agents, and Vasodilators, Vasopeptidase Inhibitors, Salines, Insulins, Blood factors, Thrombolytic agents, Hormones, Haematopoietic growth factors, Interferons, Interleukin-based products, Vaccines, Monoclonal antibodies, Tumour necrosis factors, Therapeutic enzymes, Antibody-drug conjugates, Biosimilars, Erythropoietin, Immunoglobulin, Blood and Blood components, Allergenics, Somatic cells, Gene therapy, Tissues, and Recombinant therapeutic proteins. The liquid may be any other medicament existing or in development capable of being injected into animals or humans.

An injector as described above may further comprise an external casing or housing. The casing or housing may itself comprise features such as needle shields or actuating buttons that assist in operation of the injector. The casing or housing may also be shaped to assist a user, for example the casing or housing may be ergonomically shaped.

Injections for different medicaments may require different volumes of drug to be delivered. If using conventional autoinjectors a separate autoinjector is required for each pre-filled syringe size. Advantageously, an injector as described above may be used to deliver a wide range of liquid volumes. The liquid contents are pressurised by the pressurising means whether the collapsible container is filled to capacity, only half filled, or filled to a low percentage of capacity. By varying the fill volumes, a single size of injector may be used to deliver a wide range of liquid volumes.

Conventional syringes and autoinjectors tend to be unsuited to the delivery of viscous drug solutions. The pressure required to deliver a viscous solution through an injection means such as a needle may be high and there is a risk that a syringe may break under such high pressures. The use of an injector as described above, preferably an injector in which the collapsible container is a collapsible bag or bellows, may overcome problems associated with delivery of viscous drugs. Where the collapsible container is filled with a viscous liquid, the pressurising means, for example a spring, may apply a high pressure to the viscous liquid to enable it to be delivered. The high pressure does not need to act on a delicate glass syringe and, thus, the injector may be more suitable for delivery of viscous liquids.

The invention may provide a method of injecting a liquid, the liquid being retained under pressure within a collapsible container of an injector by a normally-closed valve, the method comprising the steps of positioning the injector to deliver the liquid to a predetermined position, and opening the normally-closed valve, such that the liquid is injected. Preferably, the liquid is a liquid medicament, and the injector is positioned to deliver the liquid medicament into a patient by injection.

Once in position, for example, once a needle of the injector has been inserted into a patient's vein or elsewhere within a patient's body, the normally-closed valve may be opened manually by actuating a switch. This configuration allows a user to deliver the liquid contents of the injector only when he or she is satisfied that the injector is correctly positioned.

Where an injection is made using a conventional auto-injector, the liquid tends to be maintained at atmospheric pressure during storage before use. On activation, a plunger applies a pressure to the liquid to effect injection. The sudden application of pressure causes an initial pressure spike that may cause discomfort to a patient. The pressure spike may also be extreme enough to cause breakage of a syringe. Furthermore, where a plunger is depressed, stiction between the plunger and the syringe barrel may cause a fluctuating pressure profile during injection. The use of an injector or method of injection as described above may considerably alleviate these problems. As the liquid is maintained under pressure, there is no pressure spike when the injector is actuated. Furthermore, embodiments that use a collapsible bellows or similar collapsible bag will not suffer from the effects of stiction during delivery.

The method may comprise the step of the normally-closed valve being opened automatically when the injector is correctly positioned for delivery. For example, the injector may comprise a needle, and the normally-closed valve may be actuated when the needle has been inserted into the patient to a predetermined depth. Thus, the injector may comprise an actuator that is set to automatically open the normally-closed valve when the injector has been positioned in a predetermined position.

Preferably, the injector used in the method of injecting a liquid is an injector having any feature or combination of features described above.

The invention may further provide a method of manufacturing an injector for delivering a liquid, for example a liquid medicament, the method of manufacturing comprising the steps of coupling a normally-closed valve to a collapsible container, opening the normally closed valve, filling the collapsible container with the liquid through the normally-closed valve causing the collapsible container to expand and deflect a pressuring means, closing the normally-closed valve to retain the liquid within the collapsible container, the liquid being pressurised due to a force exerted on the collapsible container by the pressuring means, and coupling the normally-closed valve to an injection means for delivering the liquid from the collapsible container.

Many conventional auto-injectors have a staked needle. The liquid drug is, therefore, in contact with the needle during storage. By filling an injector through a normally-closed valve and then attaching a needle downstream to the normally-closed valve, the needle is maintained in a dry condition during storage before use and cannot, therefore, react with the liquid medicament during storage.

The liquid is preferably a liquid medicament.

Advantageously, the method may further comprise the step of applying a vacuum to the collapsible container through the normally-closed valve in order to remove air trapped within the collapsible container and the normally closed valve prior to filling. The removal of air may help prevent oxidation of the liquid or the undesirable solution of gases from the air into the liquid.

Preferably, the normally-closed valve is flushed with a sterilising fluid, for example ethanol, prior to coupling with the injection means.

The injector is preferably an injector having any feature or combination of features described above.

The injector may comprise a rigid container, and the method may further comprise the step of removing the air from the rigid container or flushing the rigid container with an inert gas such as nitrogen. The inert gas may be sealed within the rigid container with the collapsible container and the pressurising means. A vacuum may be applied to the rigid container by known "under the cup" vacuuming techniques or the rigid container may be evacuated via a vent defined through the walls of the rigid container.

The rigid container may contain a vent for allowing gas within the rigid container to be expelled during filling of the collapsible container. The method may further comprise the step of sealing the vent after filling in order to retain sterility and/or minimise contact between the air and the collapsible container.

Injectors according to preferred embodiments contain only a small number of component parts relative to many conventional auto-injectors. The low number of component parts and technical simplicity of preferred embodiments allows the cost per unit to be reduced relative to conventional auto-injectors.

SPECIFIC EMBODIMENTS OF THE INVENTION

Figure 2:
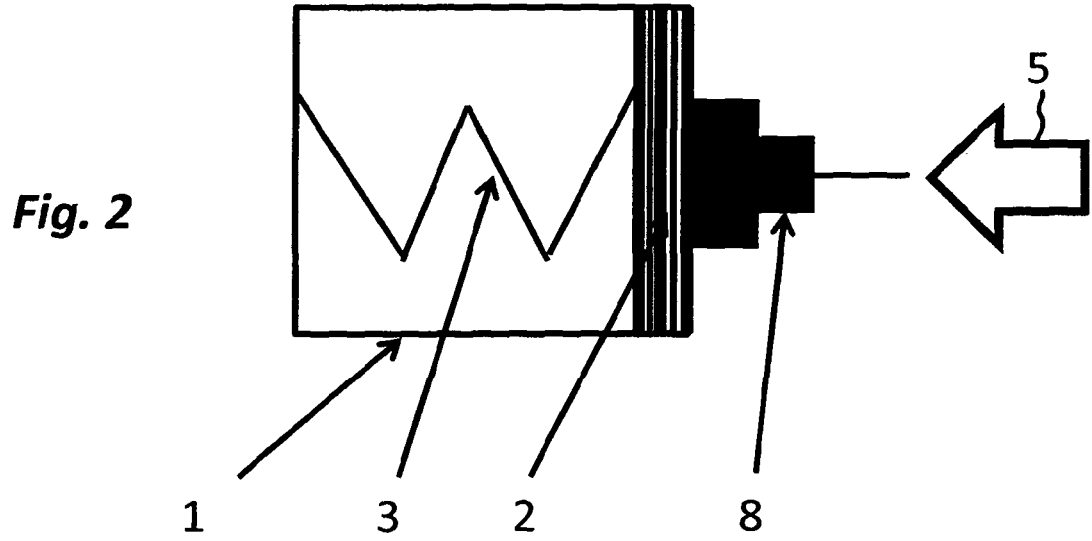
Figure 3:
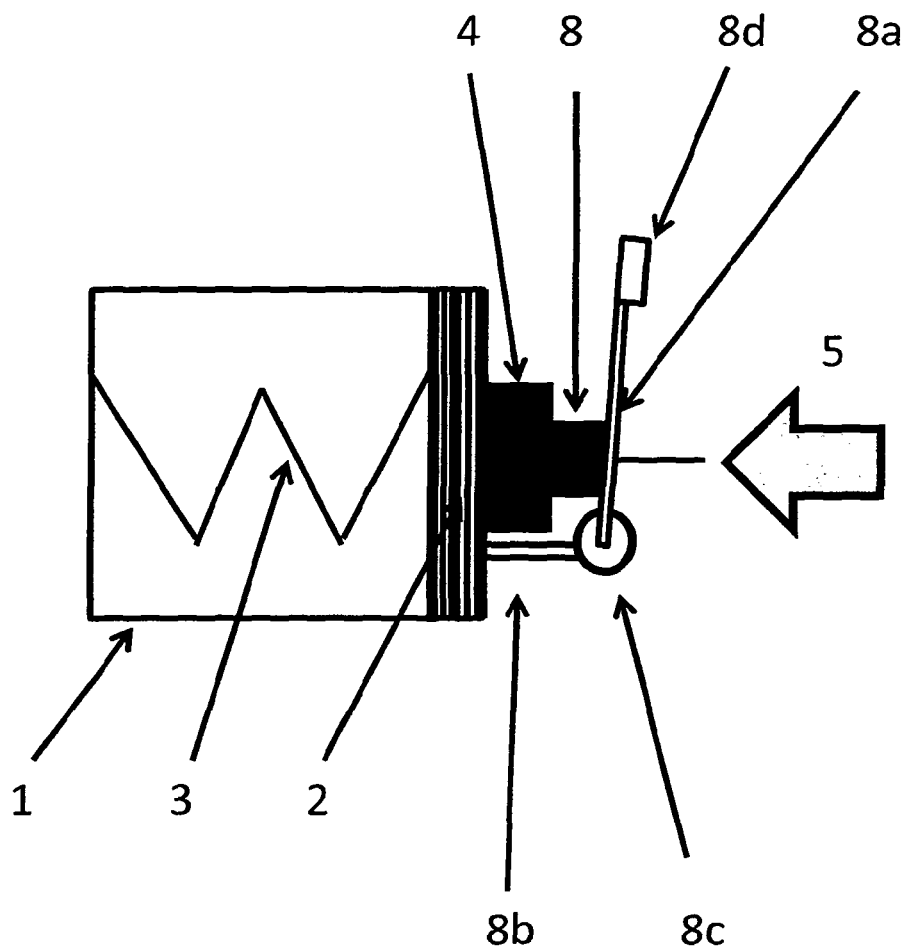
Figure 4:
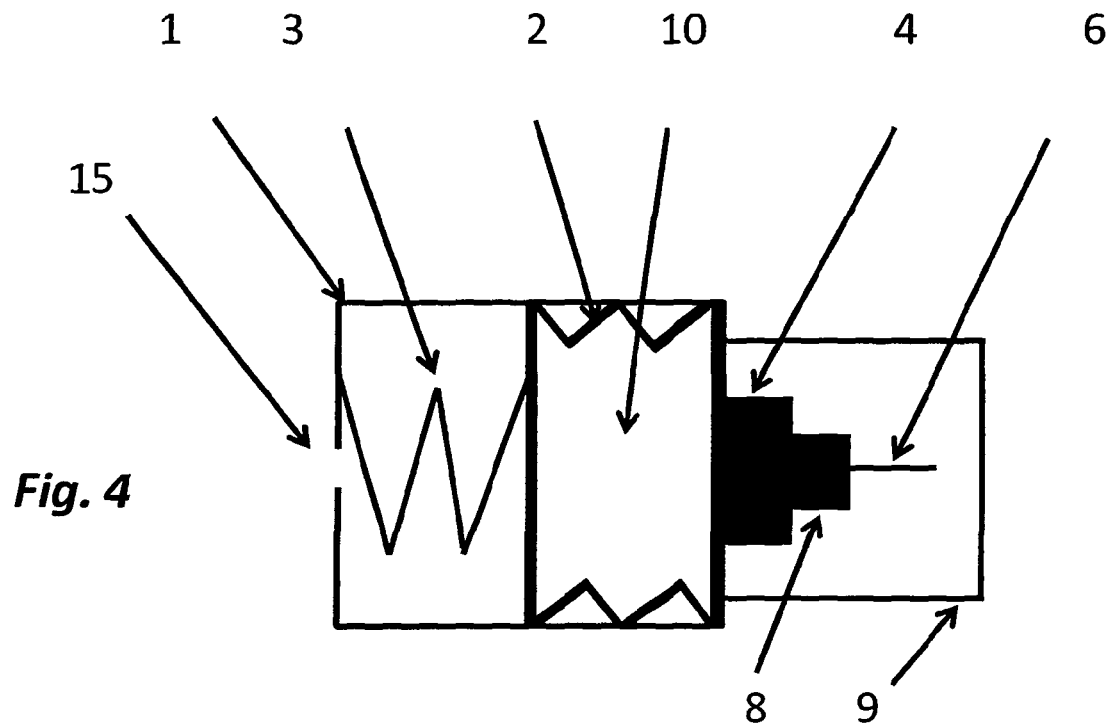
Figure 5:
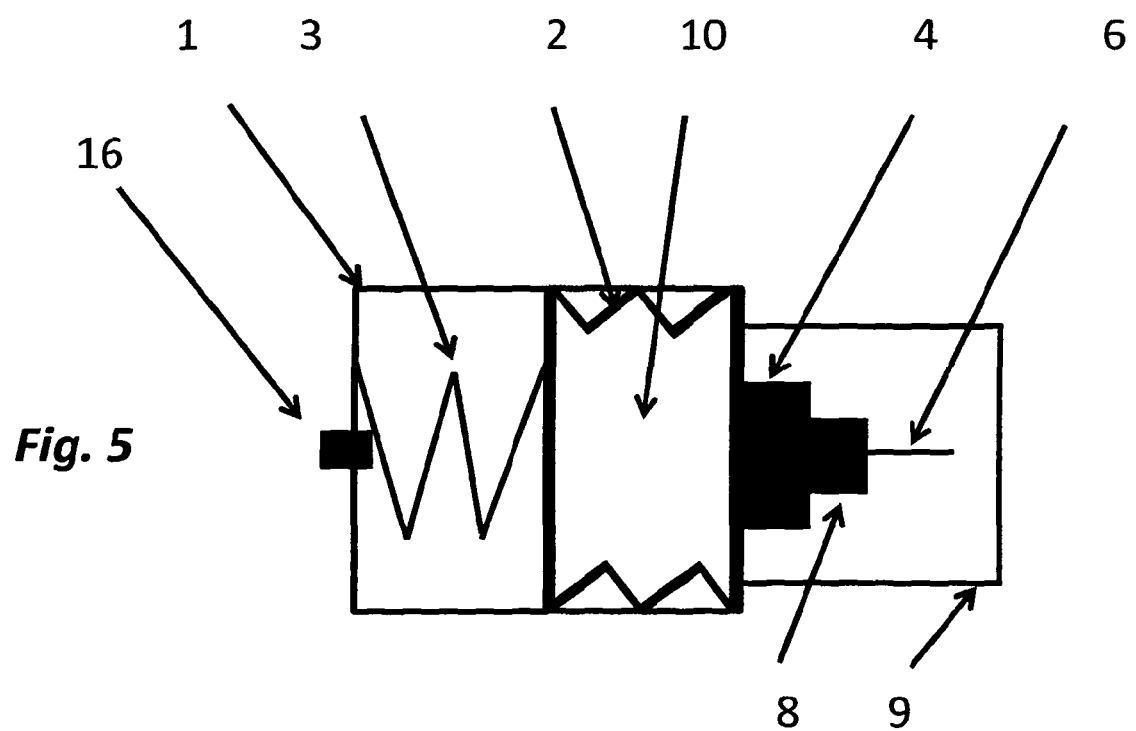
Figure 6:
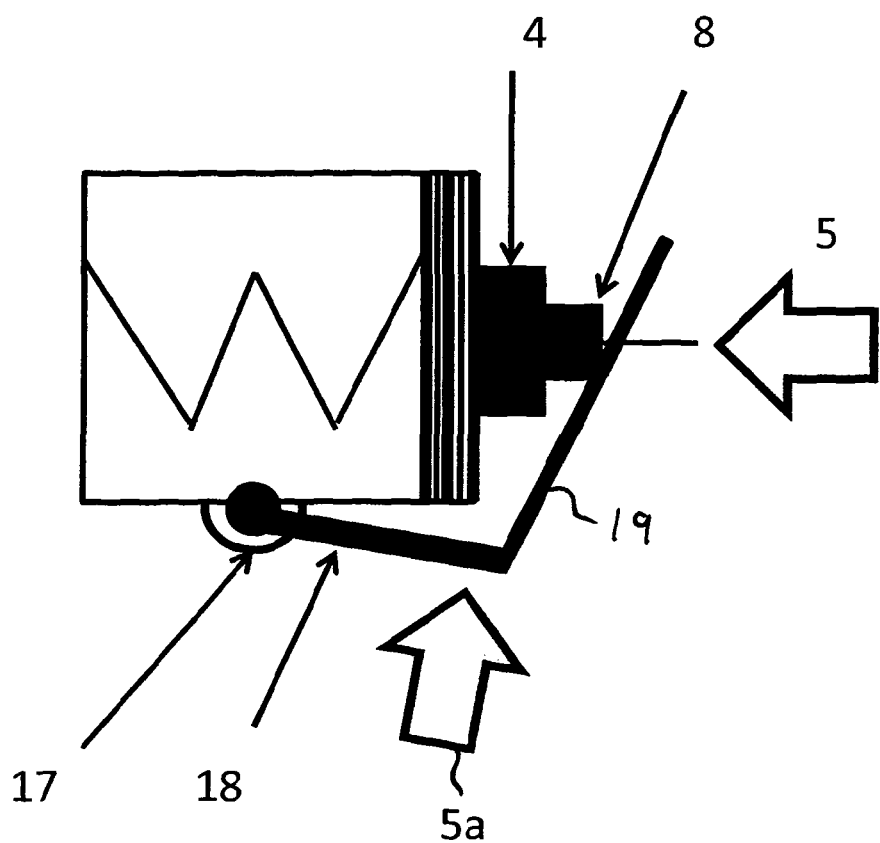
Figure 7:
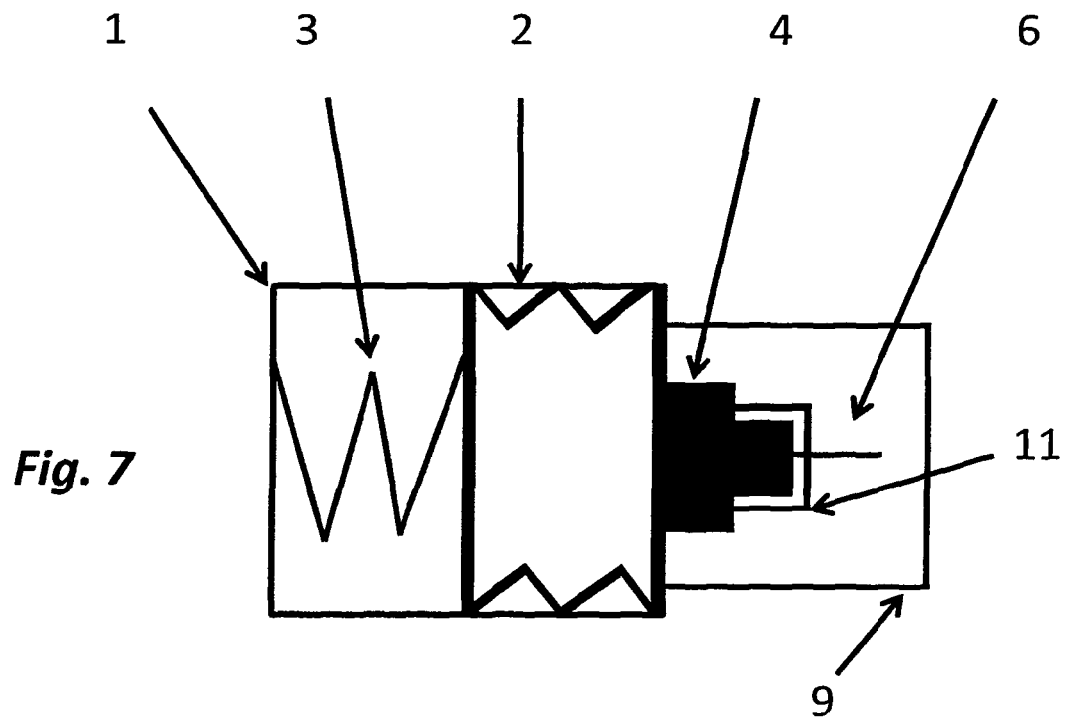
Figure 8:
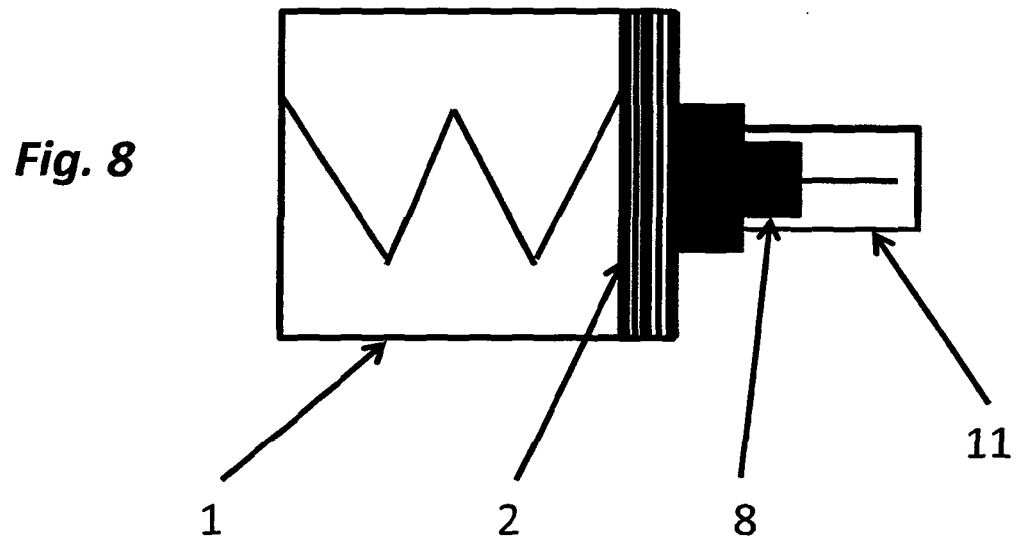
Figure 9:
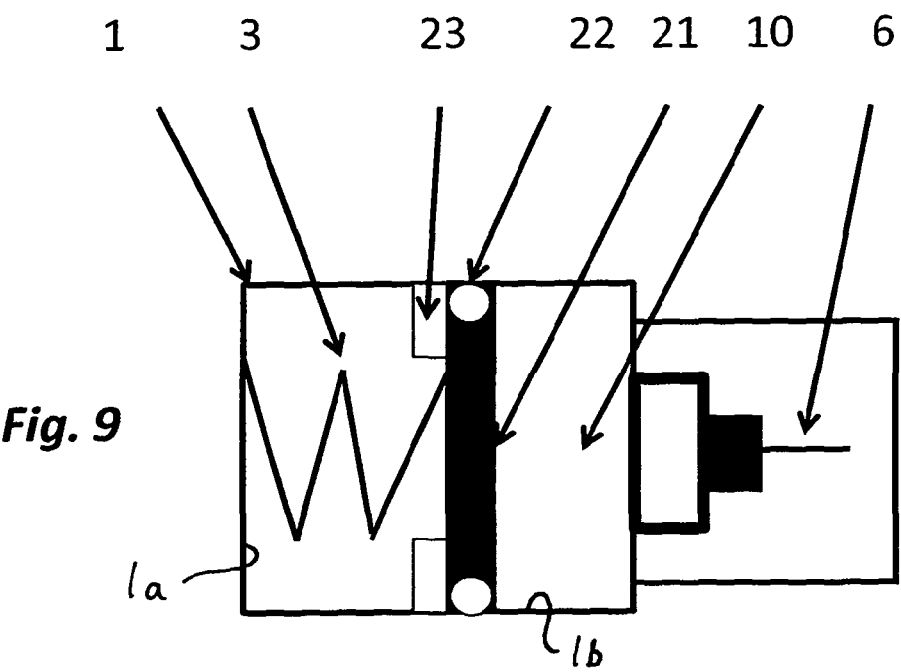
Figure 10:
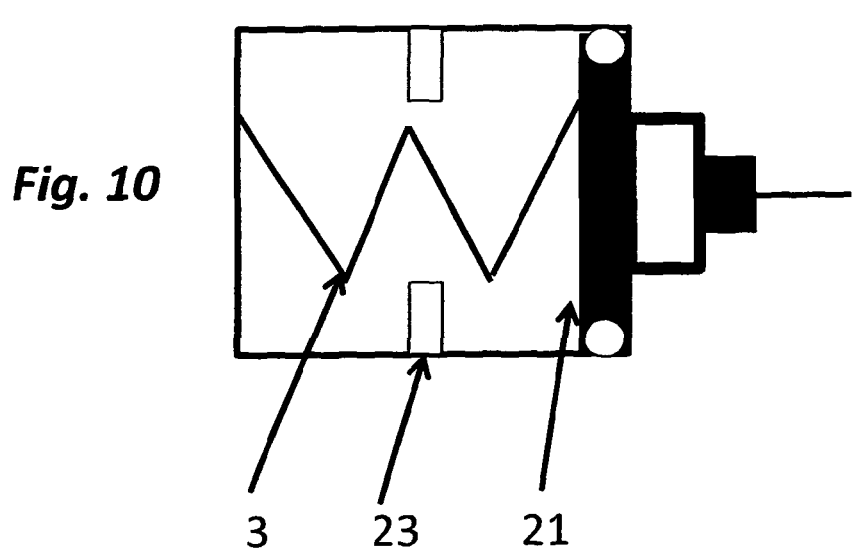
Figure 11:
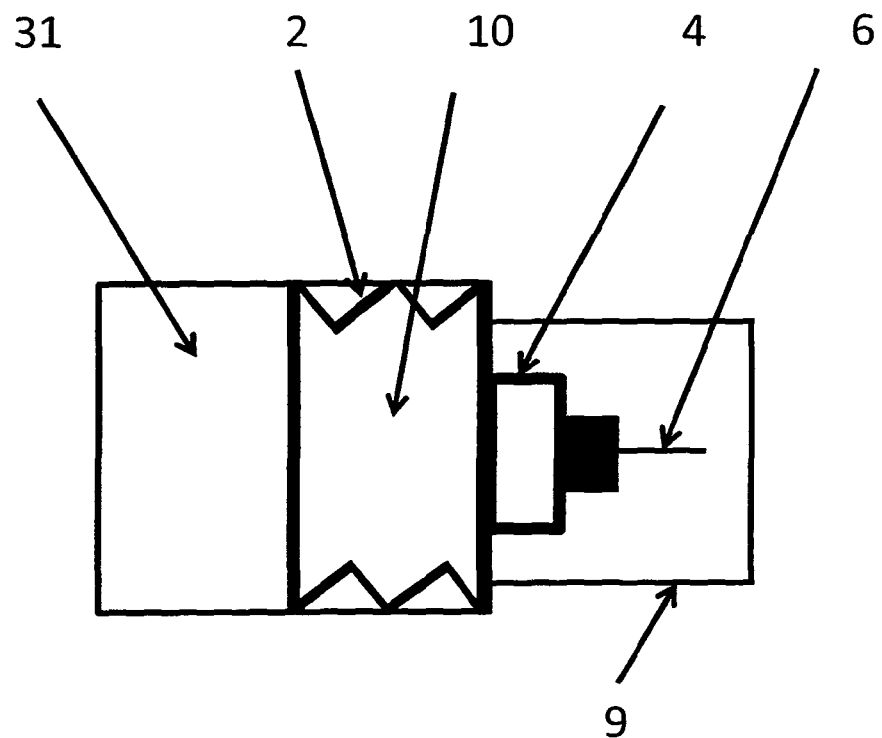
Figure 12:
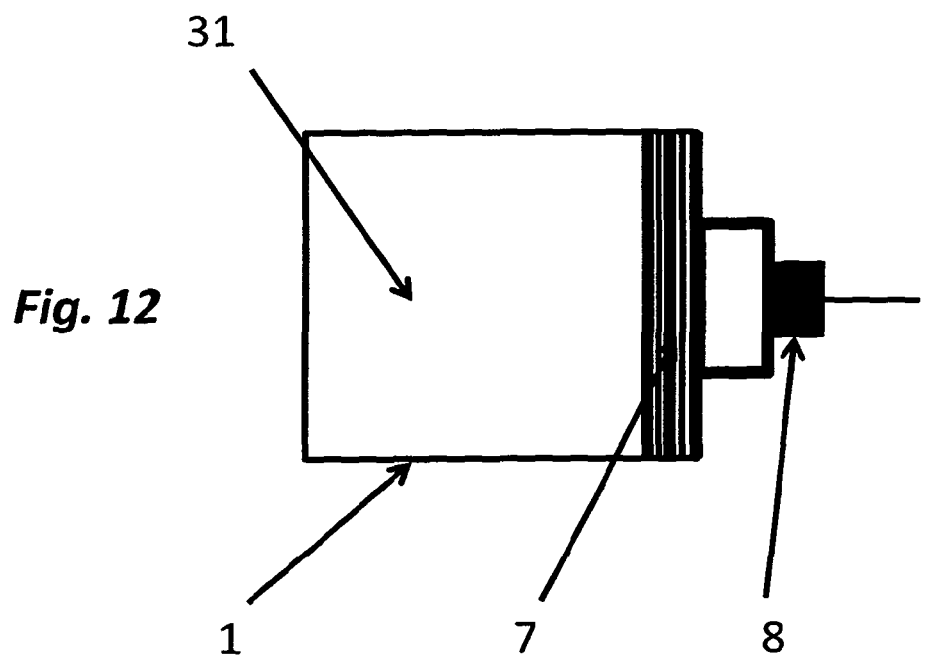
Figure 13:
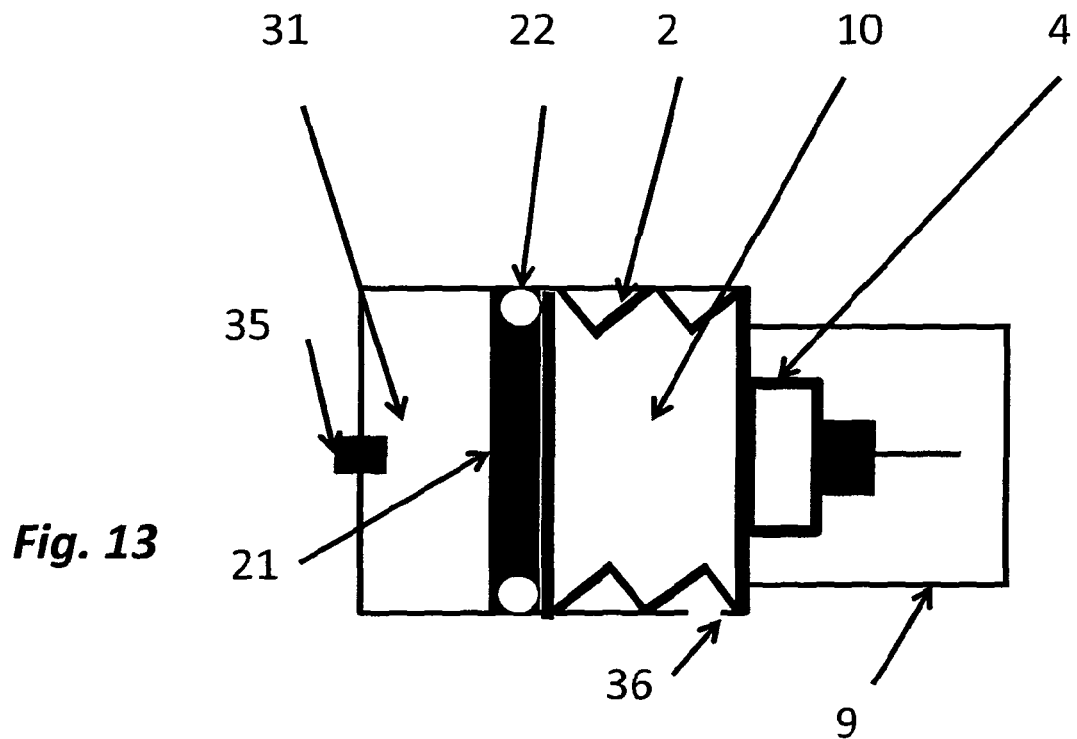
Figure 14:
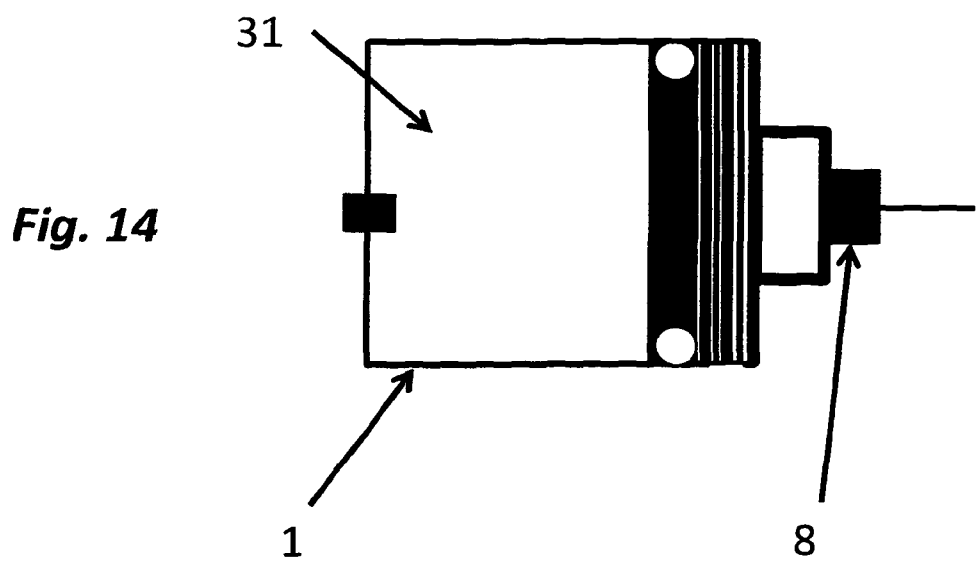
Figure 17:
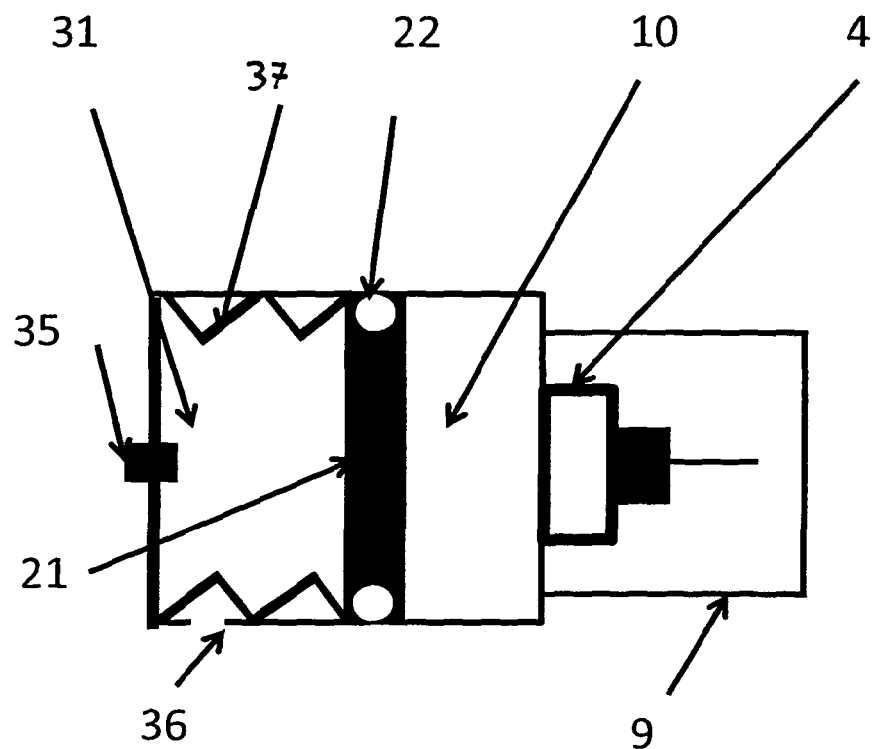
Figure 18:
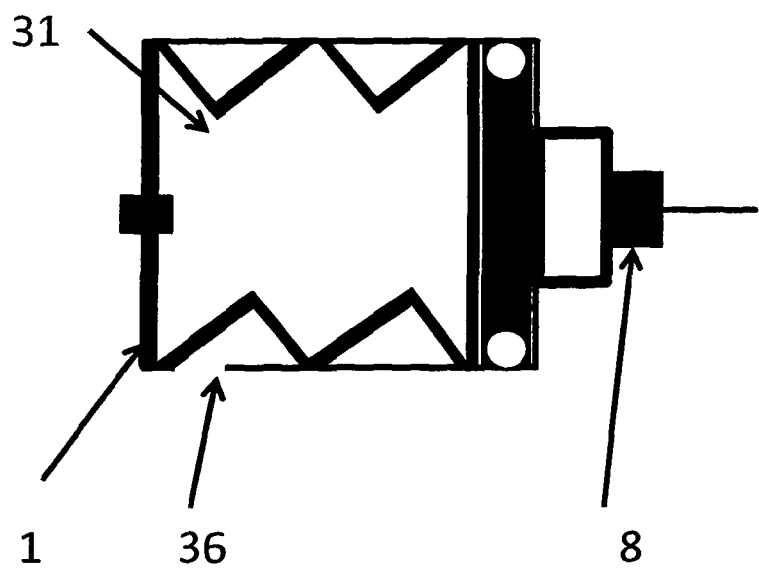
Figures 19, 20, 21:
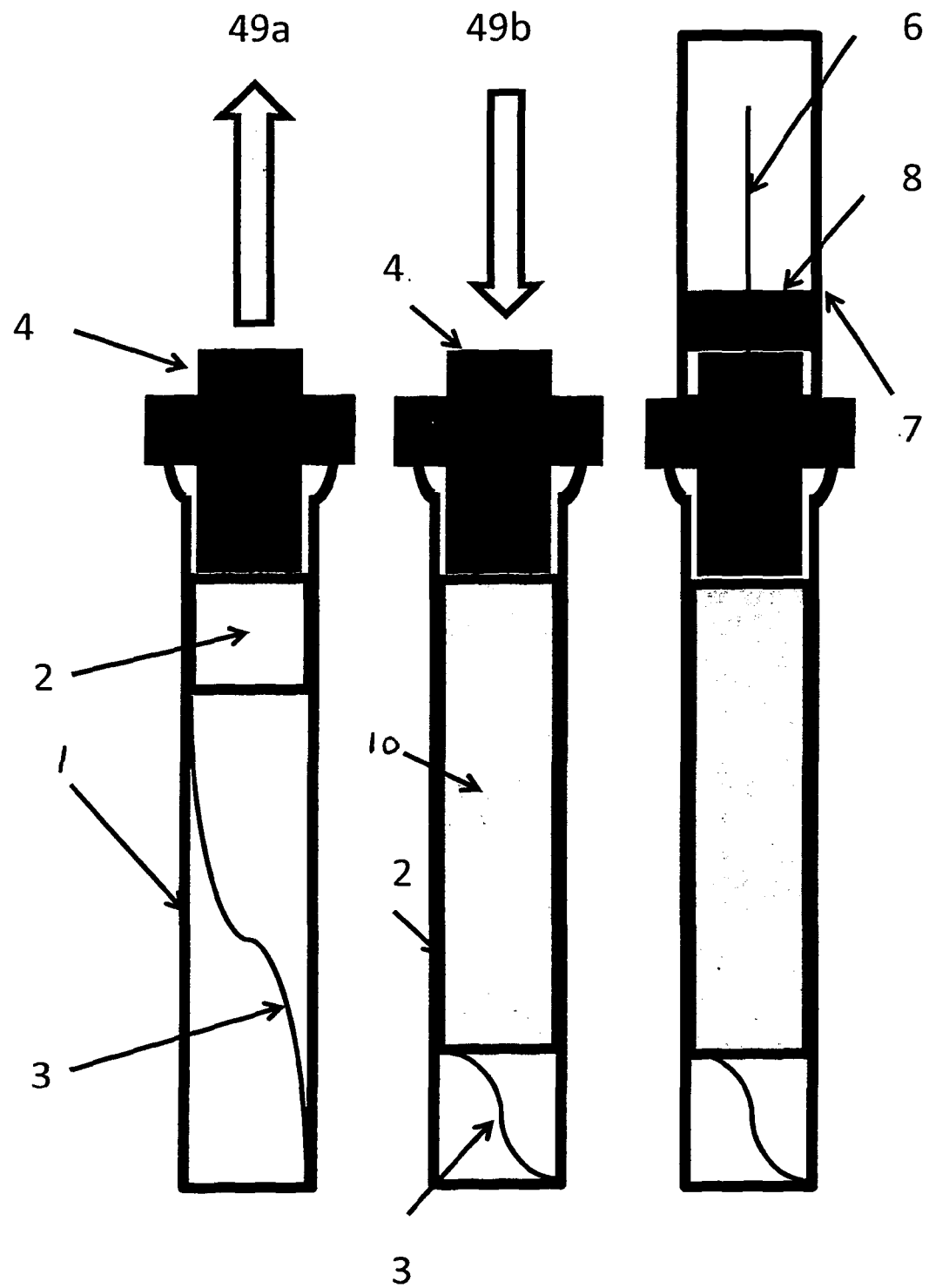
Figures 22, 23, 24:
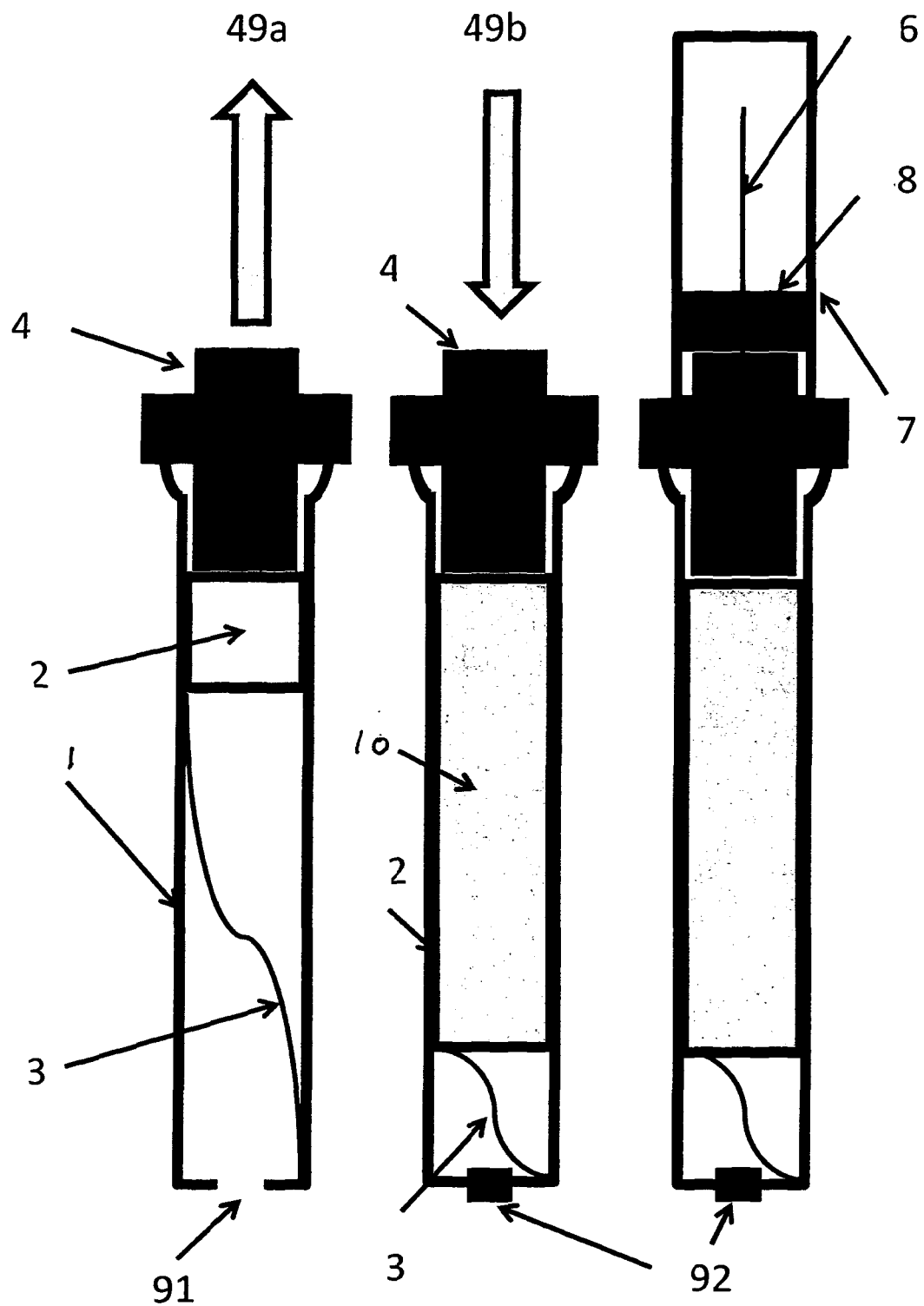
Figure 27:
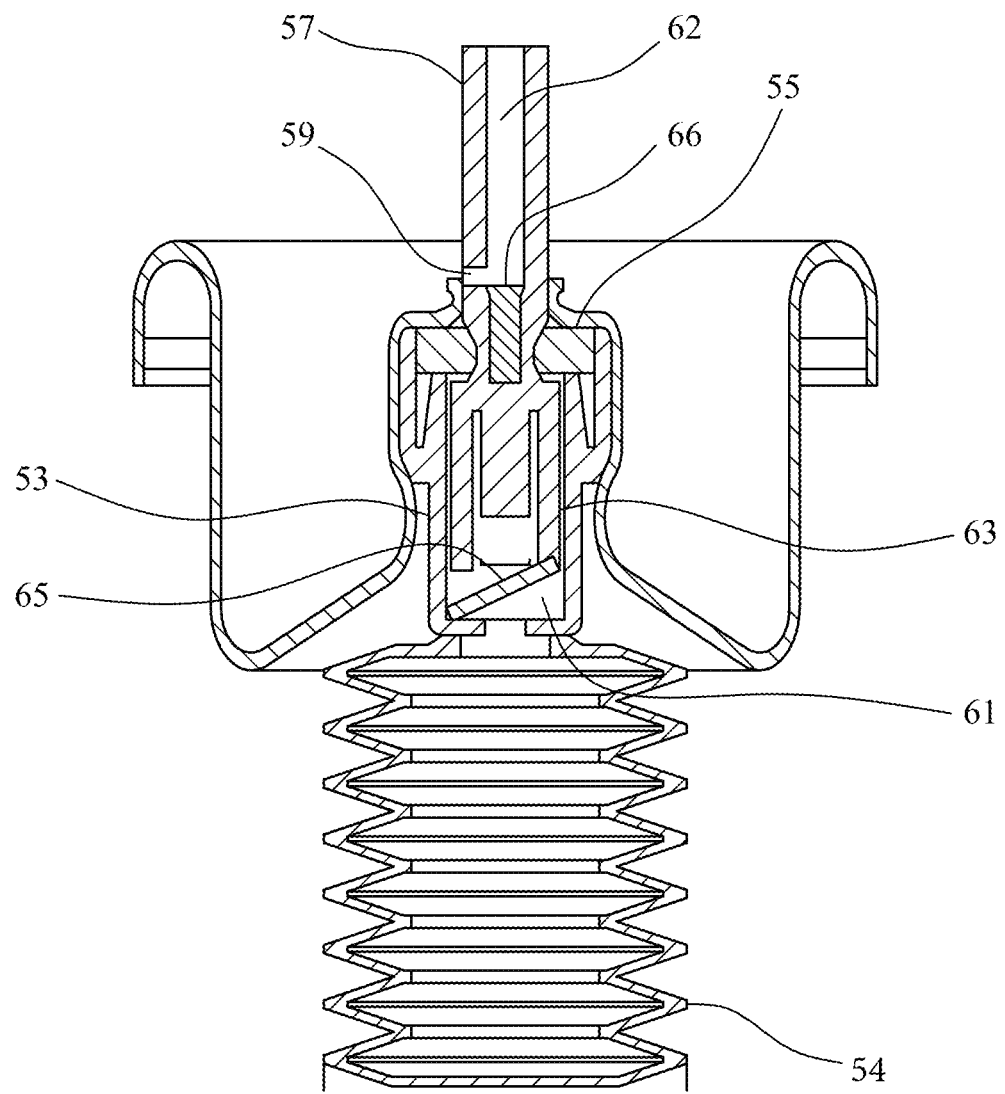
Figure 28:
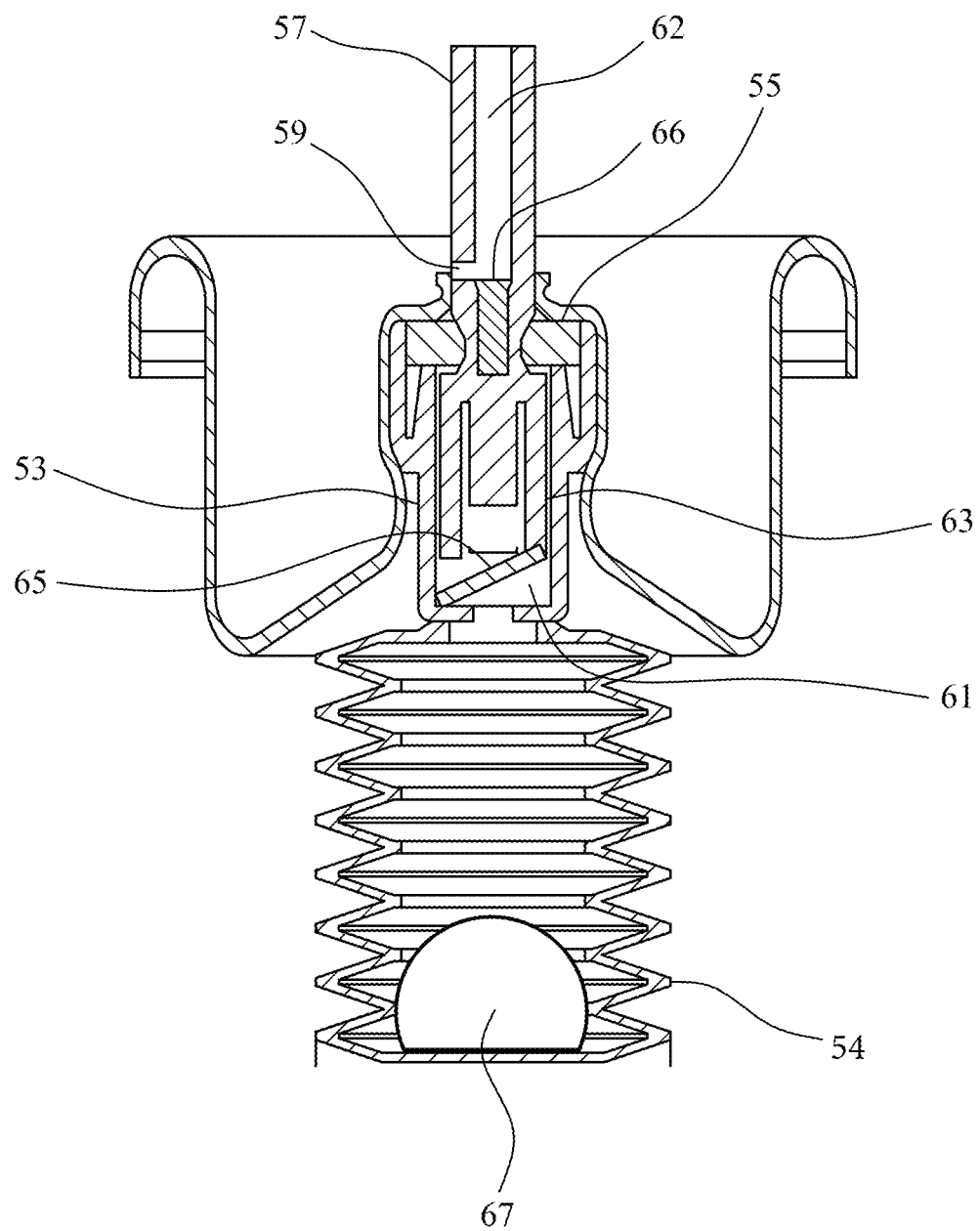
Figure 29:
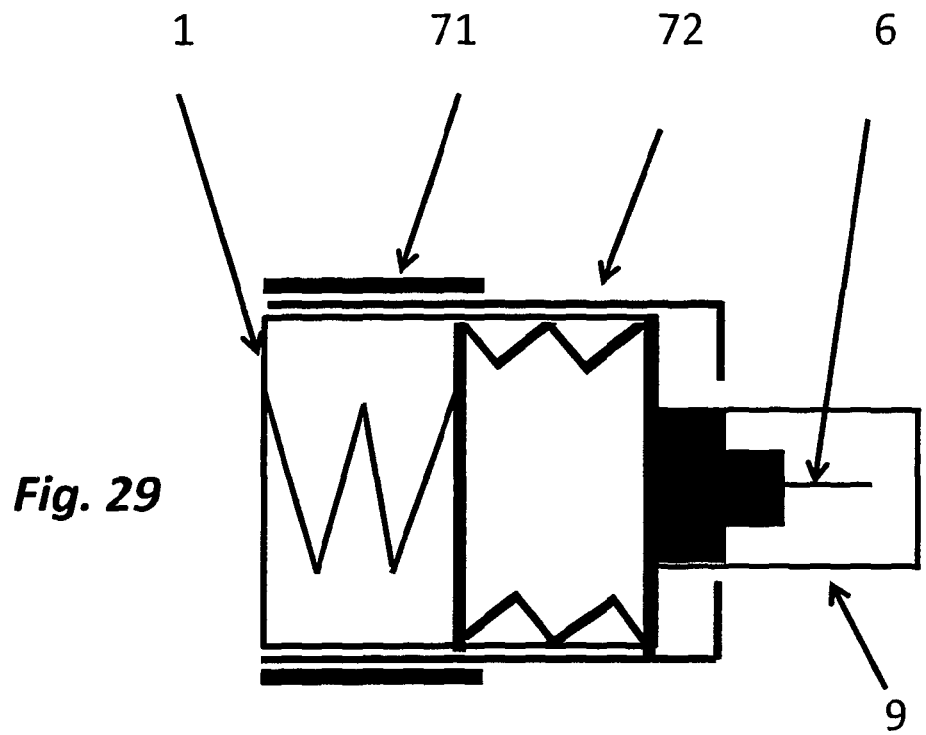
Figure 30:
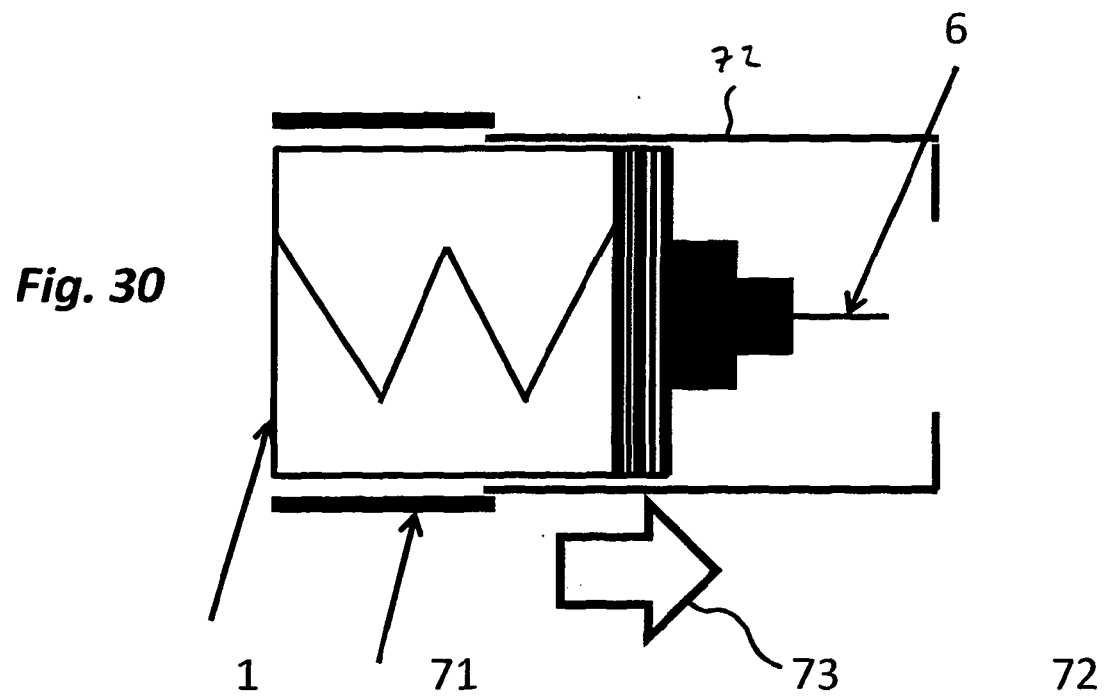
Figure 31:
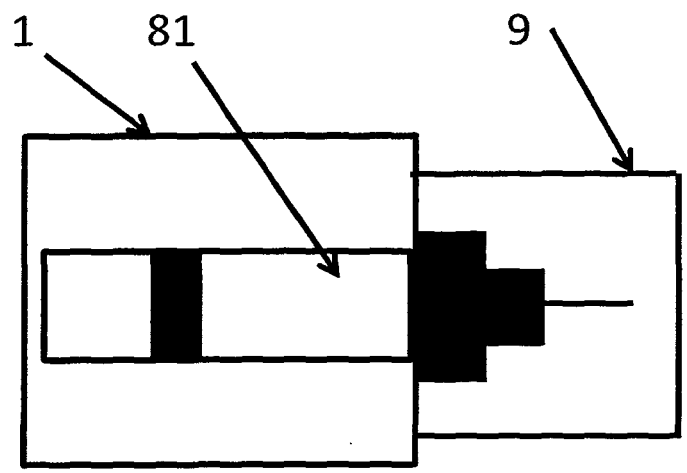
Figure 32:
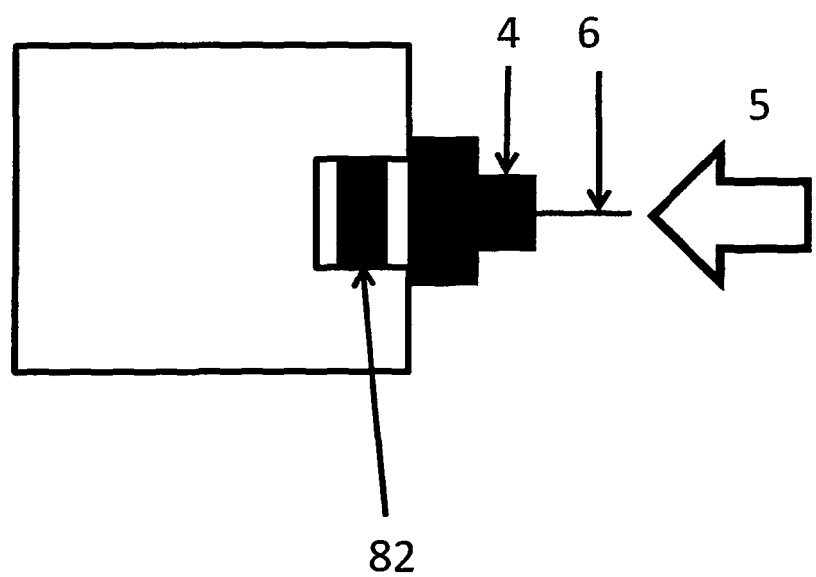
Figure 33:
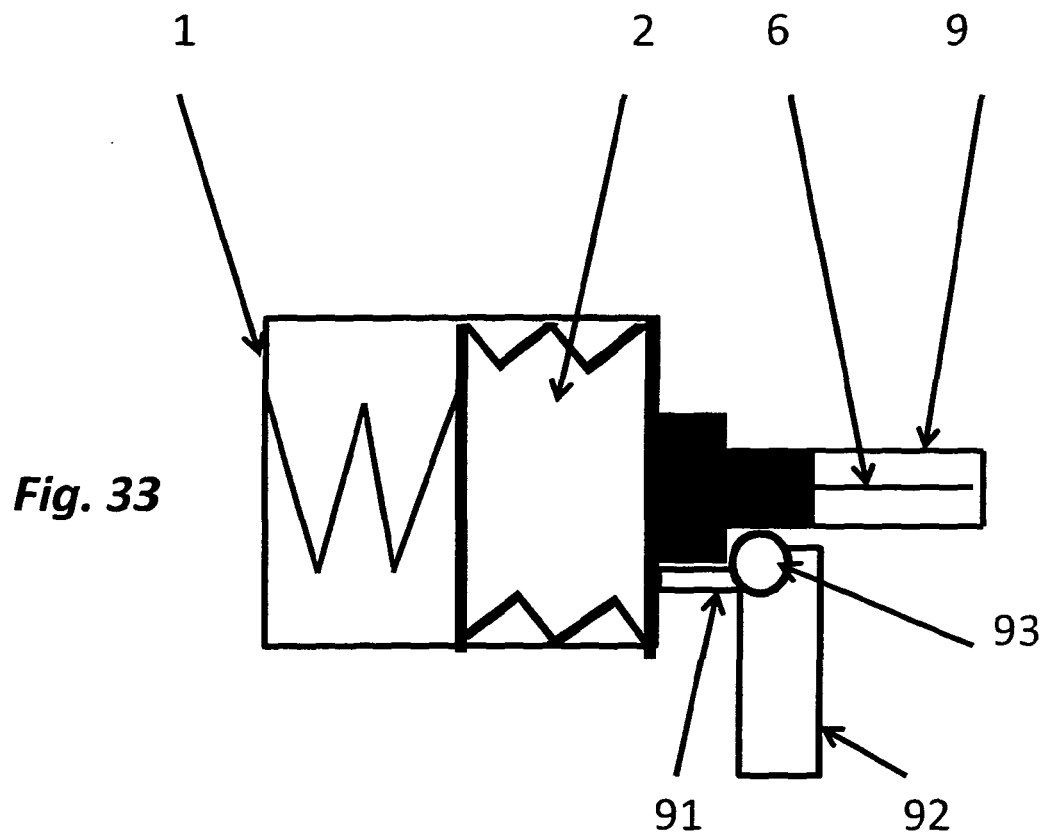
Figure 34:
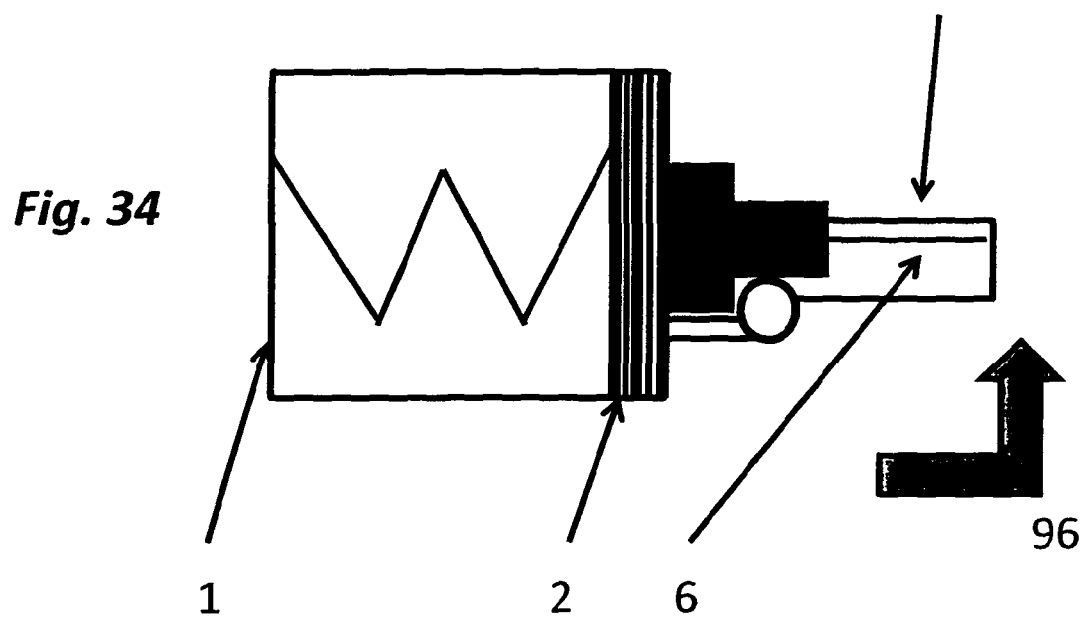
Figure 35:
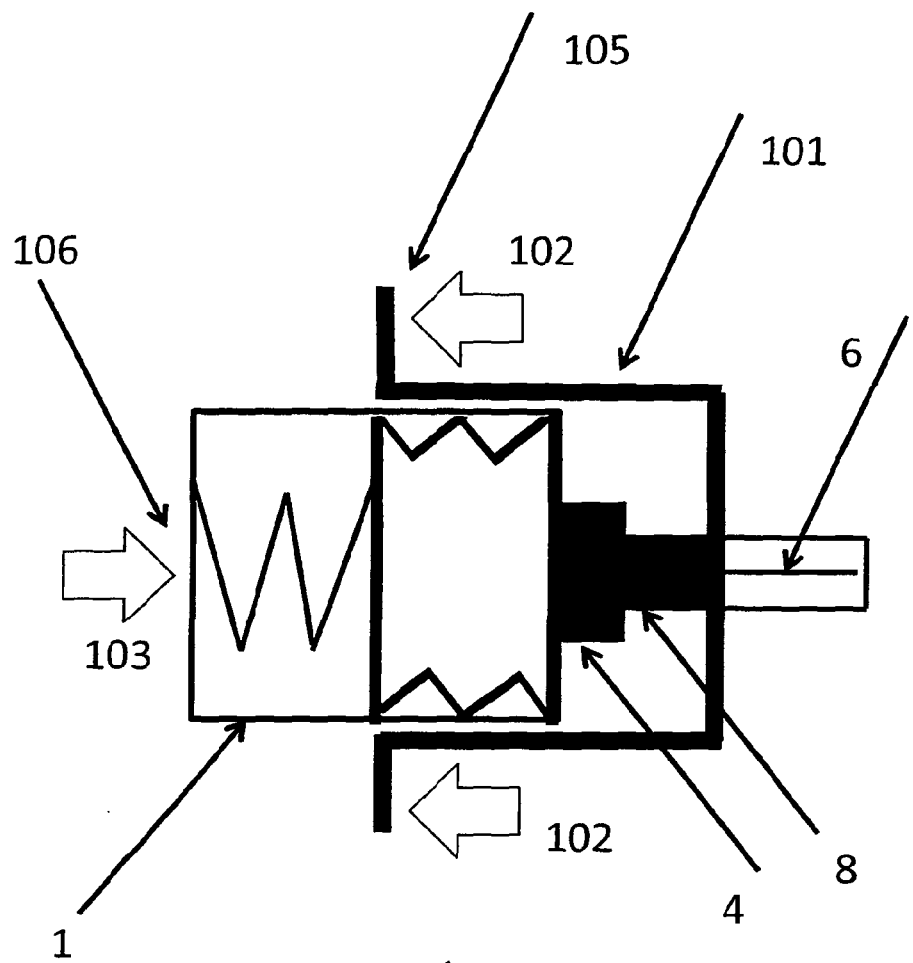
Figure 36:
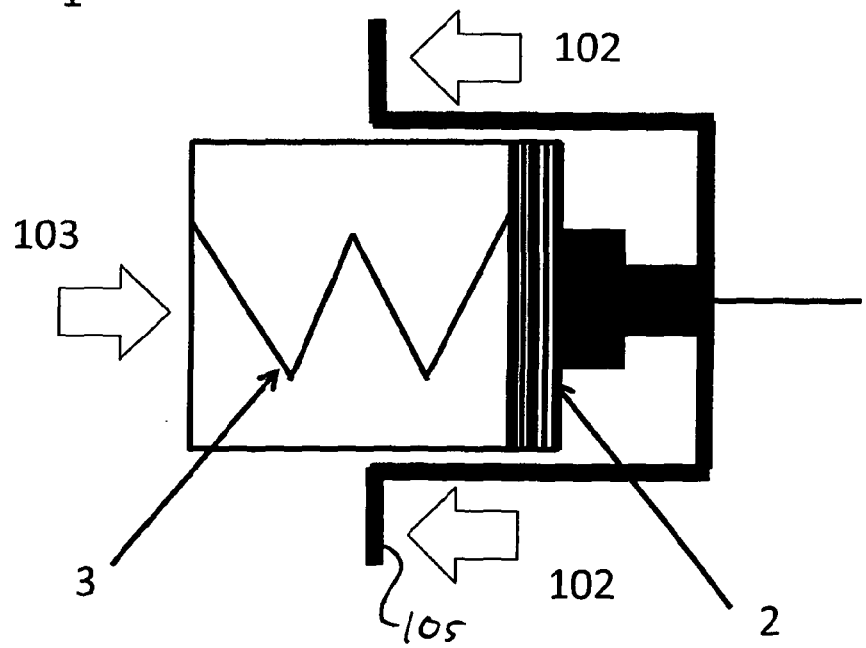
Figure 37:
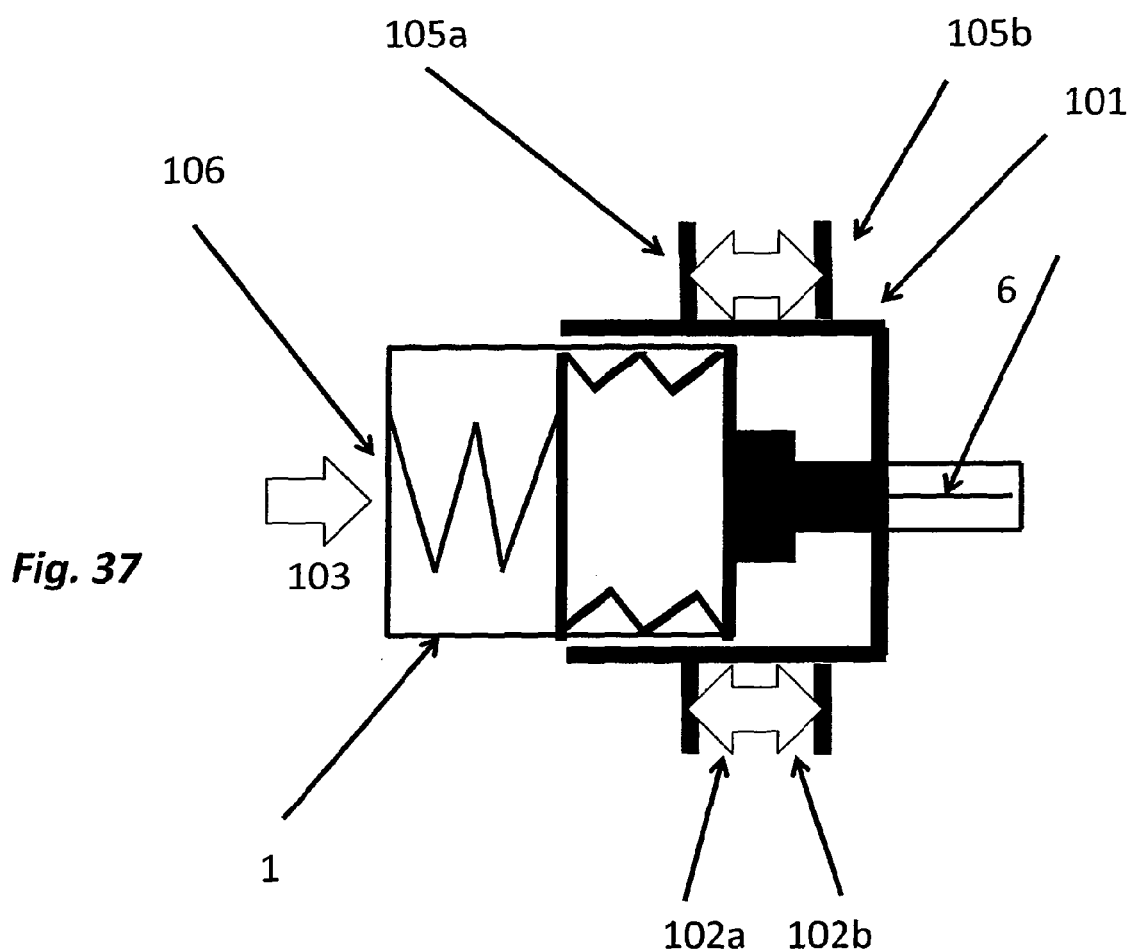
Figure 38:
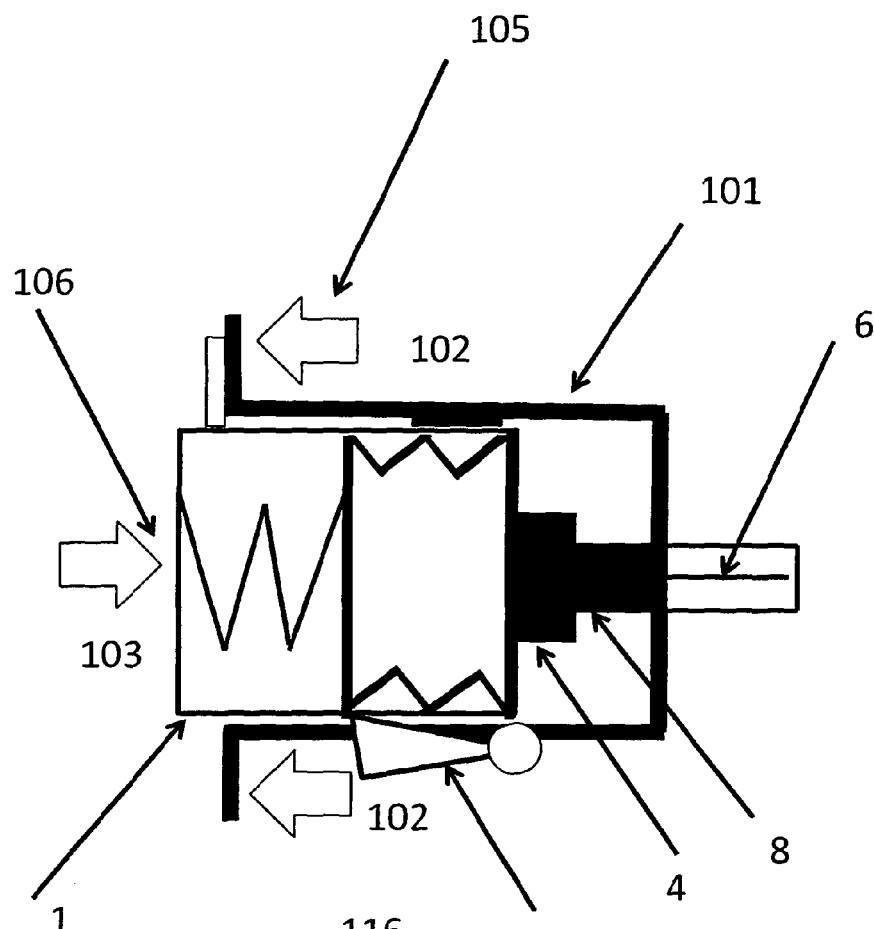
Figure 39:
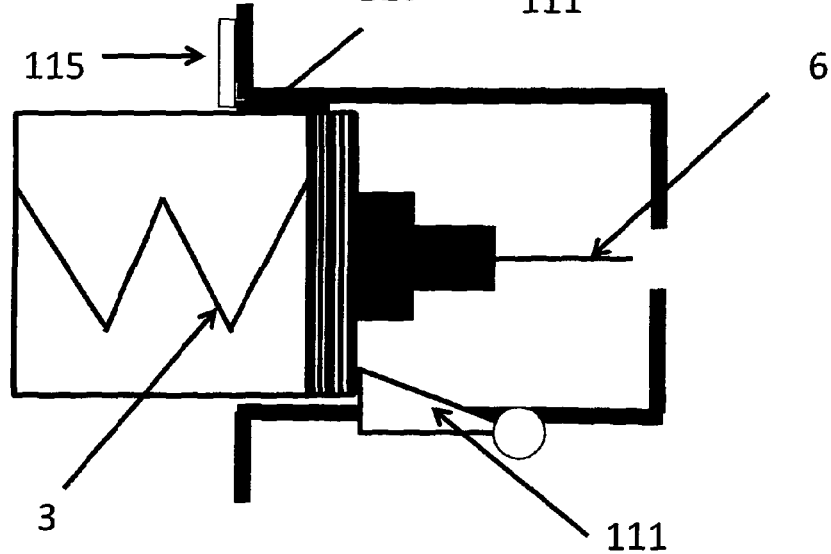
Figure 40:
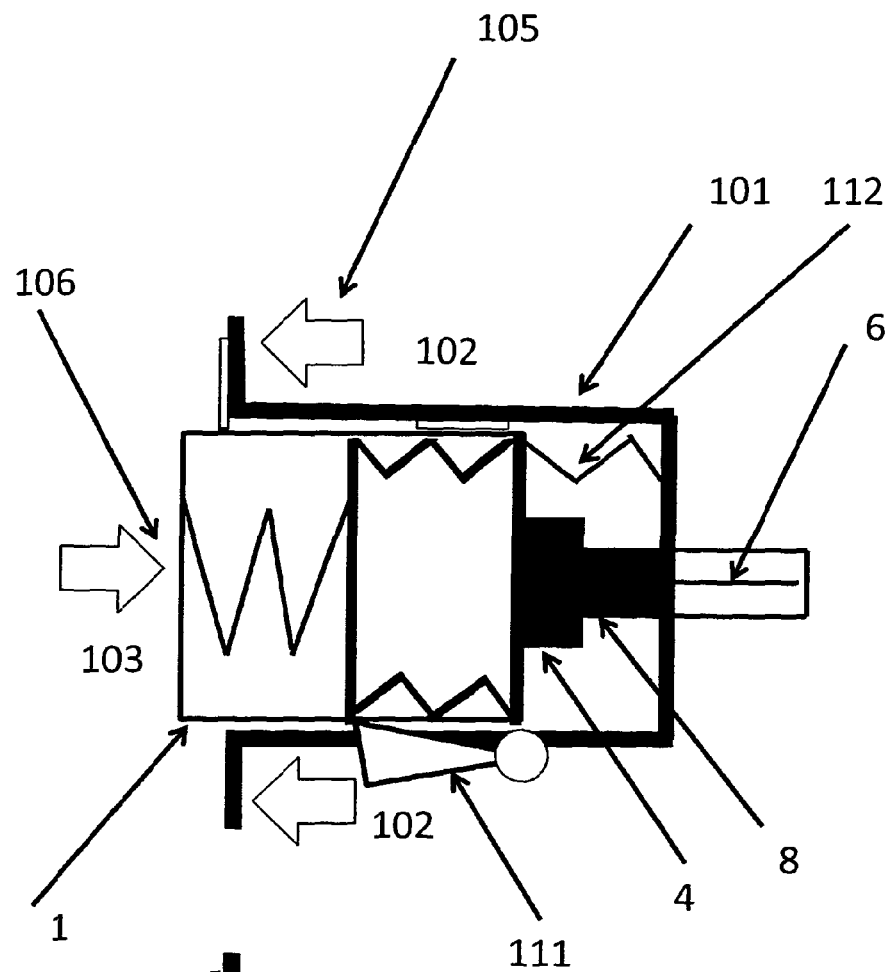
Figure 41:
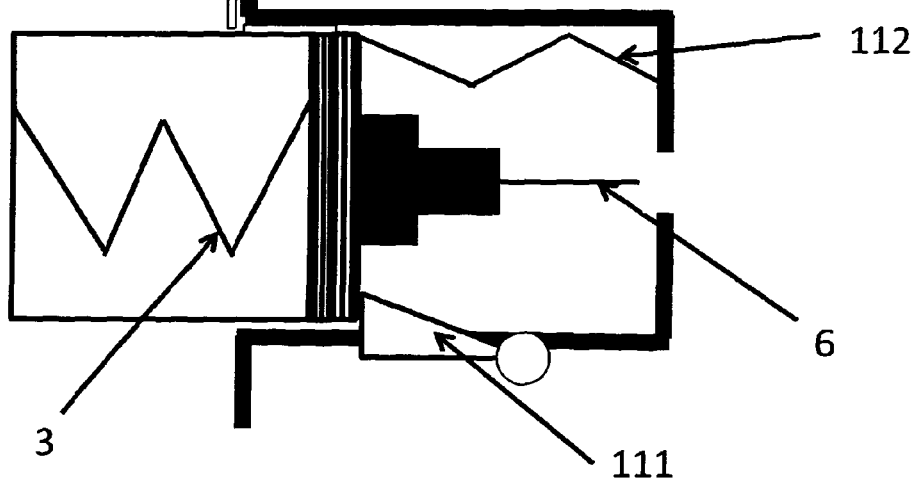
Figure 42:
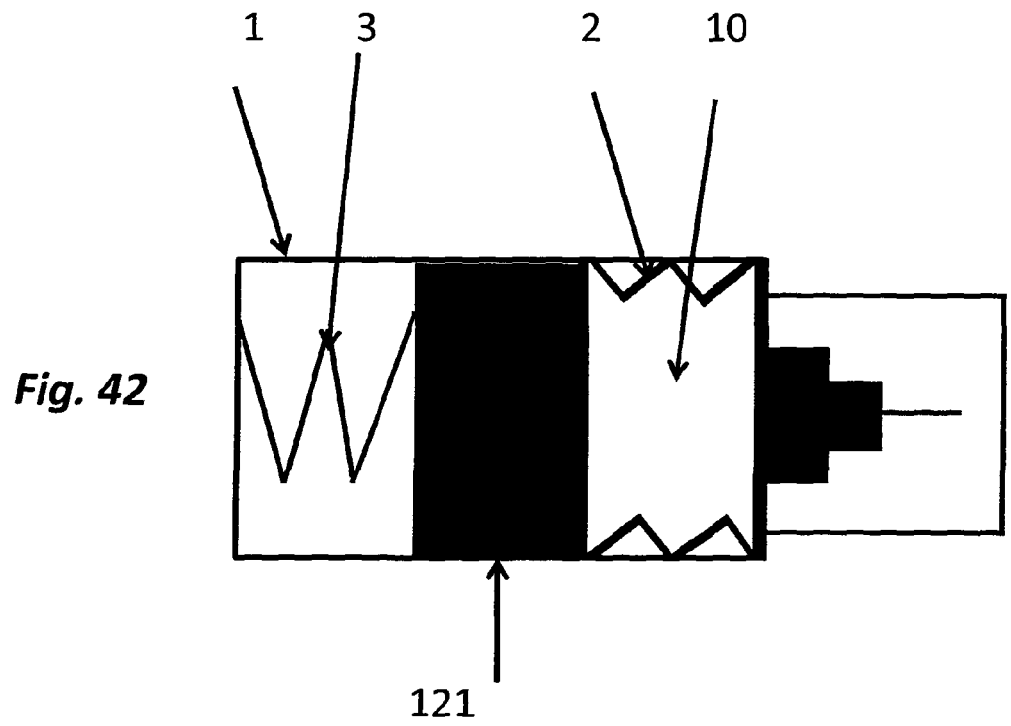
Figure 43:
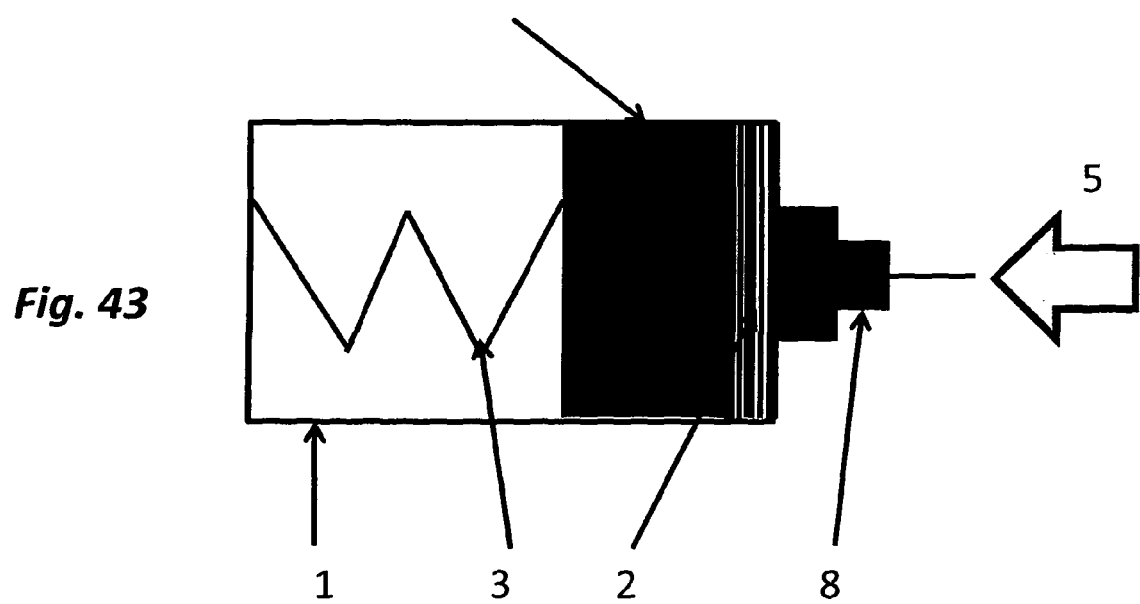
Figure 44:
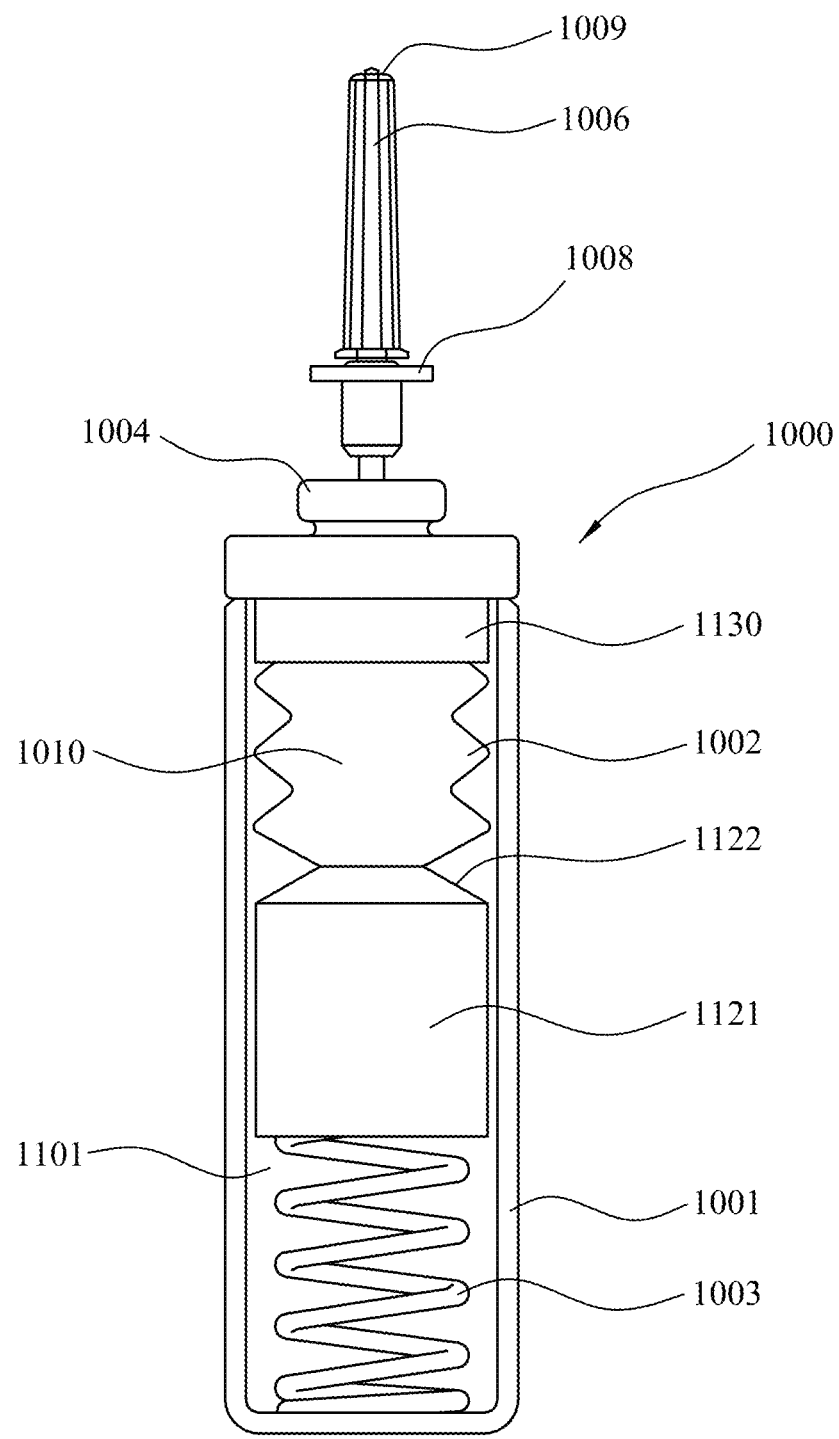
Figure 45:
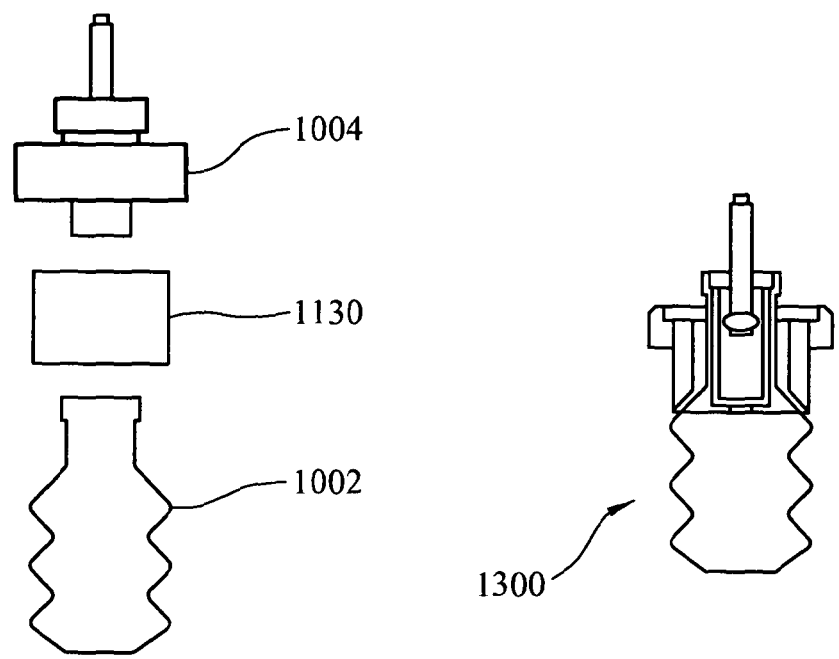
Figure 46:
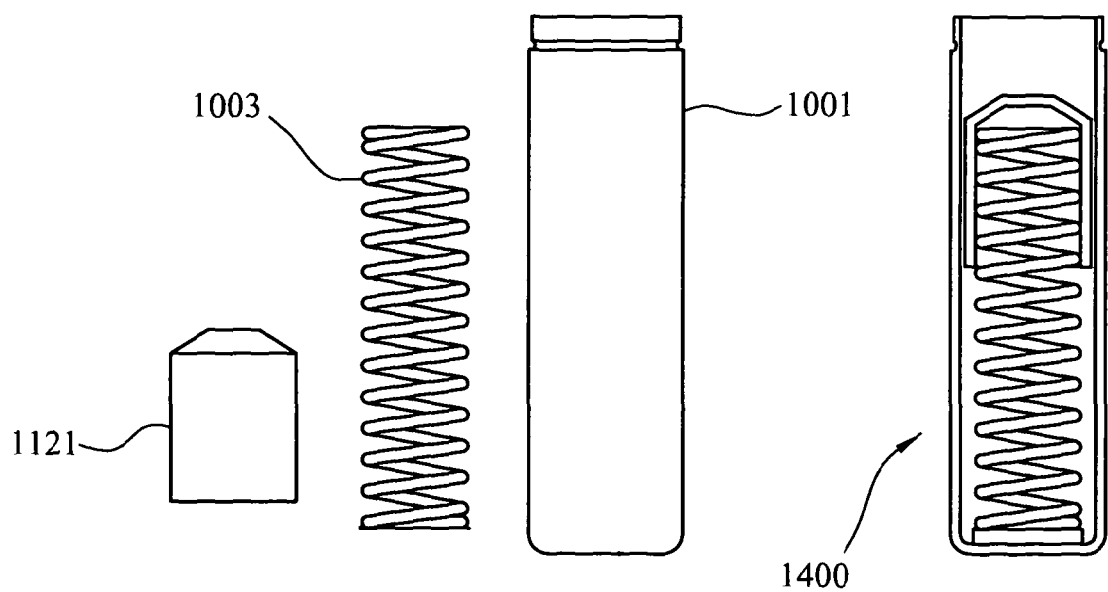
Figure 48:
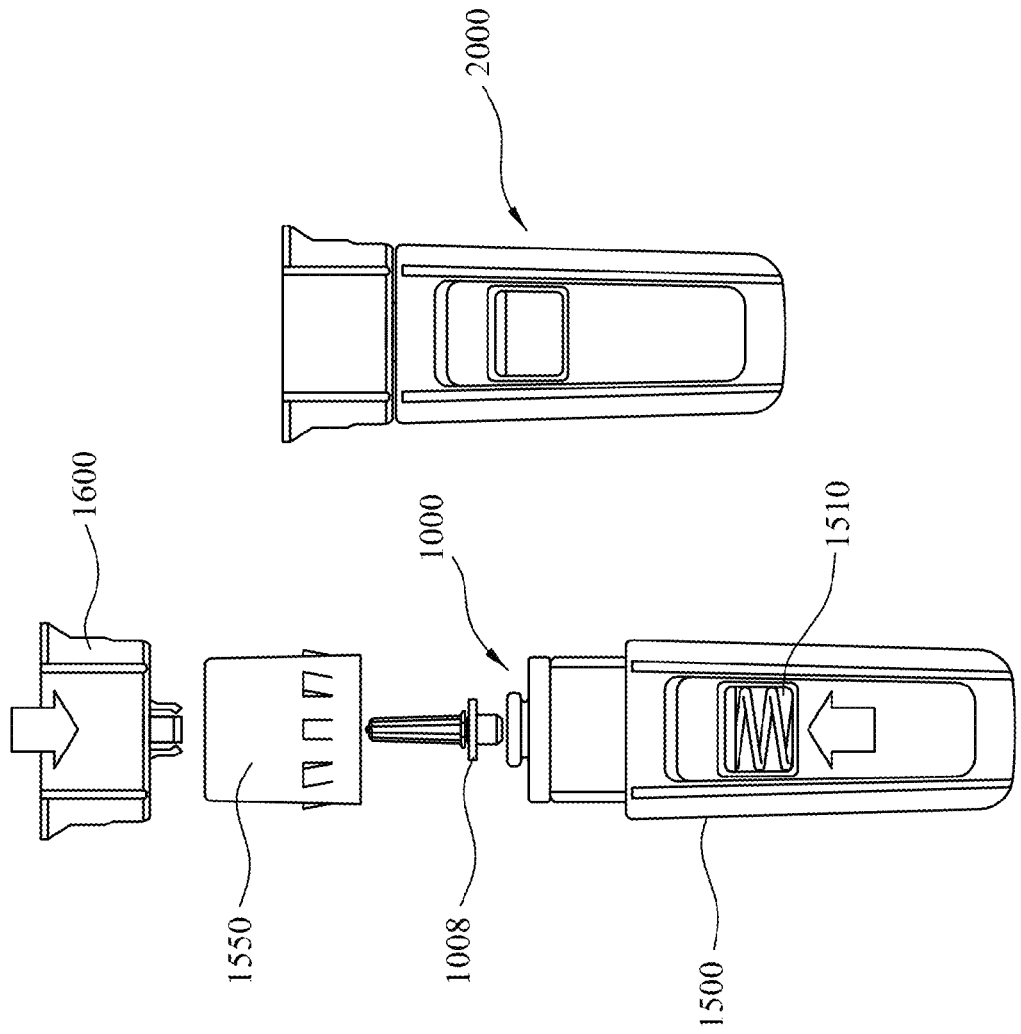
Figure 47:
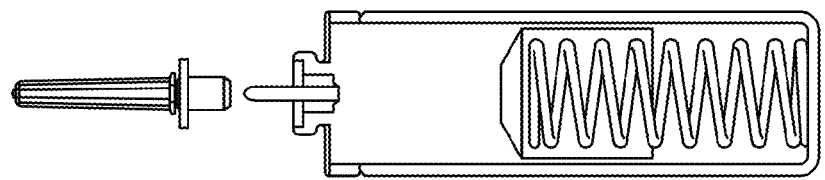
Figure 49:
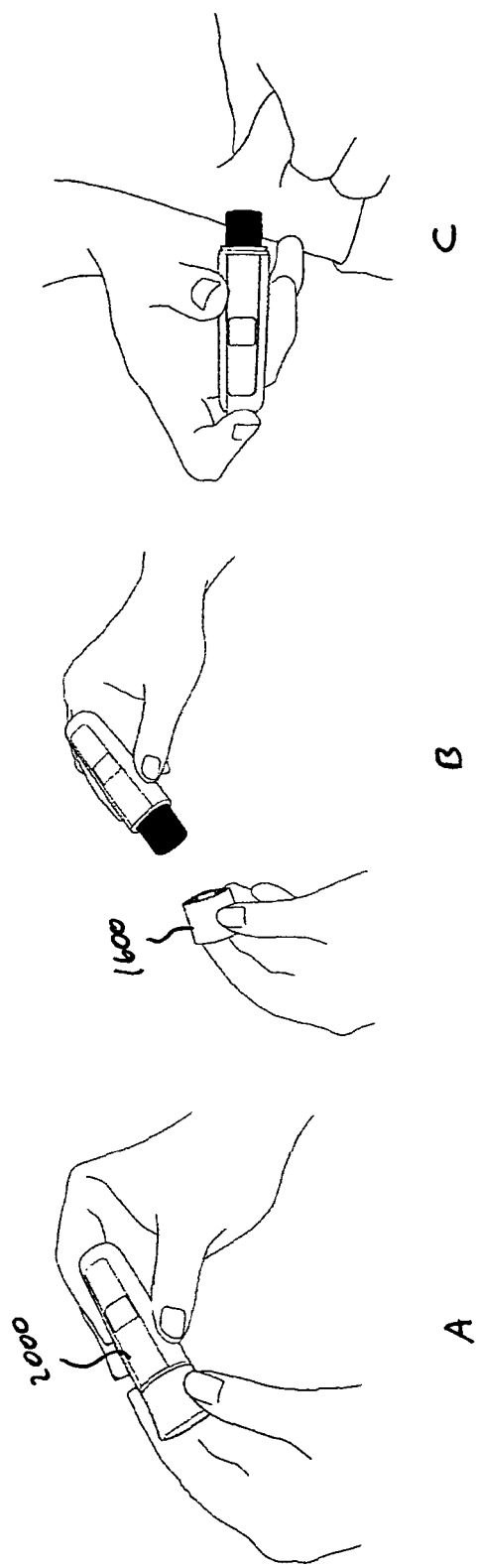

The invention will now be described with reference to the figures in which;

FIGS. 1 and 2 are schematic illustrations of an injector according to an embodiment of the invention, FIG. 3 is a schematic illustration of an injector according to an embodiment of the invention, FIGS. 4 and 5 are schematic illustrations of an injector according to an embodiment of the invention, FIG. 6 is a schematic illustration of an injector according to an embodiment of the invention, FIGS. 7 and 8 are schematic illustrations of an injector according to an embodiment of the invention, FIGS. 9 and 10 are schematic illustrations of an injector according to an embodiment of the invention, FIGS. 11 and 12 are schematic illustrations of an injector according to an embodiment of the invention, FIGS. 13 and 14 are schematic illustrations of an injector according to an embodiment of the invention, FIGS. 15 and 16 are schematic illustrations of an injector according to an embodiment of the invention, FIGS. 17 and 18 are schematic illustrations of an injector according to an embodiment of the invention, FIGS. 19, 20 and 21 illustrate the filling of an injector according to an embodiment of the invention, FIGS. 22, 23 and 24 illustrate the filling of an injector according to an embodiment of the invention, FIGS. 25, 26, 27, and 28 illustrate normally-closed valves suitable for use in an injector according to an embodiment of the invention, FIGS. 29 and 30 are schematic illustrations of an injector according to an embodiment of the invention, FIGS. 31 and 32 are schematic illustrations of an injector according to an embodiment of the invention, FIGS. 33 and 34 are schematic illustrations of an injector according to an embodiment of the invention, FIGS. 35 and 36 are schematic illustrations of an injector according to an embodiment of the invention, FIG. 37 is a schematic illustration of an injector according to an embodiment of the invention, FIGS. 38 and 39 are schematic illustrations of an injector according to an embodiment of the invention, FIGS. 40 and 41 are schematic illustrations of an injector according to an embodiment of the invention, FIGS. 42 and 43 are schematic illustrations of an injector according to an embodiment of the invention, FIG. 44 is a cross-sectional representation of an injector according to a preferred embodiment of the invention, FIG. 45 illustrates an exploded view of the component elements of a valve/bellows sub-assembly of the injector as illustrated in FIG. 44 and a cross-sectional view of the sub-assembly, FIG. 46 illustrates the component elements of a container sub-assembly of the injector illustrated in FIG. 44 and a cross-section view of the sub-assembly, FIG. 47 illustrates the attachment of a needle to form an injector as illustrated in FIG. 44, FIG. 48 illustrates the encasement of the injector as illustrated in FIG. 44, and FIG. 49 illustrates the steps required to use the encased injector illustrated in FIG. 48.

FIGS. 1 and 2 schematically illustrate the components and operation of an injector according to an embodiment of the invention. A rigid container 1 houses a collapsible bellows 2 containing a liquid drug 10 and a spring 3 for pressurising or compressing the liquid drug 10. A normally-closed valve 4 connects the liquid drug 10 contained within the collapsible bellows to a valve actuator 8 and a needle 6 for delivering the drug.

FIG. 1 shows the injector before use. The collapsible bellows 2 are filled with the liquid drug 10 and the collapsible bellows compresses the spring 3 against an internal wall 1a of the rigid container 1. In its compressed condition, the spring 3 exerts a force against both the internal wall of the rigid container 1a and the collapsible bellows 2, thereby pressurising the liquid drug 10 contained within the bellows. A cap 9 keeps the needle free from contamination prior to use. The cap 9 may be fixed to the device with a tamper evident feature.

When the injector is used, the needle 6 pierces the skin and enters the body to a predetermined depth depending on the target location. When the actuator 8 touches the skin and is pressed against it, the actuator 8 moves towards the rigid container (in the direction shown by arrow 5) thereby opening the normally-closed valve 4 and allowing the liquid drug 10 contained within the bellows 2 to flow through needle 6 under the pressure generated by spring 3. In FIG. 2 the device is shown after use with the spring 3 extended and the bellows 2 collapsed, the liquid drug contents 10 having been expelled.

The actuator 8 may comprise a device or element to gain a mechanical advantage and lower the force required to operate the actuator. An example is shown in FIG. 3. In the embodiment of an injector illustrated in FIG. 3, the actuator 8 is coupled to an arm 8a. The arm 8a has a raised portion 8d, which when acted on by a patient's skin forces actuator 8 inwards as shown by arrow 5. The arm 8a is supported by a lug 8b and pivoted at a hinge 8c. Other arrangements are possible.

Alternatively the actuator may be pressed by a separate mechanical linkage attached to a finger button. This arrangement may be spring loaded to aid activation.

The collapsible bellows 2 may be made of any suitable plastic such as Polyethylene, ABS, Polycarbonate, Polypropylene, PPO, PET or any other plastic suitable for blow moulding and compatible with the liquid drug being stored in the bellows. The rigid container 1 may be transparent and made from for example PET plastic or other transparent material.

In FIG. 4 an embodiment of an injector is schematically illustrated in which the rigid container 1 incorporates a vent hole 15. This vent hole 15 may allow gas trapped within the rigid container 1 to escape during filling of the bellows 2.

FIG. 5 schematically illustrates an embodiment of an injector substantially the same as that illustrated in FIG. 4, but in which a plug 16 blocks the vent 15 to prevent further air entering the rigid container 1 during storage and use.

If the vent 15 is placed in the rigid container 1, then after filling the pressure within the rigid container 1 is atmospheric. If the plug 16 is inserted after filling, the pressure within the rigid container 1 will decrease as the liquid drug 10 is delivered and the collapsible bellows 2 collapse.

FIG. 6 schematically illustrates an embodiment of an injector in which the actuation of the normally-closed valve is achieved manually. In FIG. 6 a manually-actuated button arrangement is shown. A finger lever 18 is pivoted at a pivot point 17 and attached to actuation member 19. When finger pressure is applied on lever 18 in the direction of arrow 5a the actuator 8 of the normally-closed valve 4 is depressed (in the direction of arrow 5) thereby opening the normally-closed valve 4.

FIGS. 7 and 8 schematically illustrate an embodiment of an injector having an automatic or passive needle shield. A shield 11 is shown in FIG. 7 in a retracted position. In FIG. 8 the shield 11 is shown in an extended position covering the needle to prevent needle stick injuries. A passive needle shield as described in Patent US 2009/0227956A1 may be suitable, or any other type of needle shield may be used, preferable a shield which is activated automatically once the needle 6 is pulled out of the body after use. Alternatively a manual needle shield may be used which is activated by the user after use.

FIGS. 9 and 10 illustrate an embodiment of an injector in which the collapsible container is formed from a piston and cylinder arrangement rather than a collapsible bellows. Components of the injector that are common to the various embodiments of injectors described above have been given the same reference numerals. A rigid container 1 is cylindrical in shape and defined a cylindrical internal cavity. The rigid container 1 houses a piston 21 with a seal 22 that contacts an internal wall 1b of the rigid cylinder. The piston 21 and the internal walls 1b of the rigid container 1 define a collapsible chamber for containing a liquid drug 10.

Before use, the piston 21 rests against a seal 23, which may be a flexible seal or a spring loaded seal, to minimise drug evaporation and gas interchange. A spring 3 urges against the piston 21 and an end wall 1a of the rigid container, compressing the liquid contents 10 of the collapsible container and expelling them via a needle 6. The piston 21 may be associated with more than one seal 22. The piston is preferably made of a plastic or elastomer, and in some cases a separate seal 22 may not be needed.

FIGS. 11 and 12 are schematic illustrations of an injector according to an embodiment of the invention in which the means for pressurising the liquid drug 10 is provided by a gas 31. The gas 31 may be a compressed gas such as Nitrogen or Air or a liquefied gas such as HFA134a or HFA227.

In other embodiments, a combination of a spring 3 and gas 31 may be used or a combination of gases. A gas 31 may be introduced into the rigid container 1 by 'under the cup' filling or any other way.

FIGS. 13 and 14 illustrate an embodiment of an injector in which an additional piston 21 is used to further separate a pressurising gas 31 from a liquid 10 contained in collapsible bellows 2. The gas 31 is filled through hole and plug 35. A further vent 36 in the rigid container 1 ensures that any gas leak past piston seal 22 does not enter bellows 2 (which may contaminate the liquid drug) and is vented through vent 26 instead. In this way a liquefied gas such as HFA134a can be used to keep pressure on bellows 2 constant without the risk of any gas entering bellows 2 if there is a failure of seal 22.

FIGS. 15 and 16 are schematic illustrations of an injector embodiment comprising a double bellows system. A first collapsible bellows 2 contains the drug 10 and a second collapsible bellows 37 contains a compressible gas 31. The second bellows 37 may be filled via hole and plug 35. When the first bellows 2 is filled with the drug 10 as shown in FIG. 15, the second bellows and the compressible gas 31 are compressed. The compressed gas 31 provides a force that acts to pressurise the liquid drug 10 contained in the first bellows 2. When the normally-closed valve 4 is opened the compressed gas 31 is allowed to expand, thereby expelling the liquid 10 through the needle 6.

FIGS. 17 and 18 illustrate an alternative embodiment of an injector where a compressible gas 31 is stored in a collapsible bellows 37 and the liquid drug 10 is contained by a piston/cylinder type collapsible chamber as described above. A vent hole 36 in the rigid container 1 is now located near the bellows 37.

FIGS. 19 to 21 schematically illustrate the assembly and filling process of an injector of the type described above in relation to FIGS. 1 and 2. In FIG. 19 a rigid container 1 has within a collapsible bellows 2 attached to a normally-closed valve 4 and compressed by a spring 3. In the first assembly operation the spring 3 is dropped into the rigid container 1. In the second assembly operation the valve and bellows assembly is crimped to the container 1, thereby pre-compressing the spring 3.

A vacuum is then applied as shown by arrow 49a to remove air trapped in the valve and bellows.

In FIG. 20 an arrow 49b indicates the filling of contents 10 via the valve 4 into the bellows 2 thereby expanding the bellows 2 and further compressing the spring 3. If the container 1 is completely sealed with no vent hole then any gas (usually air) trapped within the container 1 is also compressed, creating an additional energy source acting to compress the bellows 2. Air may be replaced with Nitrogen before fixing valve 4 to the rigid container 1 to minimise Oxygen within the container 1 that might affect the content 10 of the bellows 2.

After filling the drug contents via the valve into the bellows 2 the liquid passageways of the valve 4 are preferably flushed with a clean liquid such as ethanol or any other suitable liquid or any suitable gas or a gas and liquid mixture or separately by both to ensure sterility before sealing with the cap 7 as shown in FIG. 21.

In FIG. 21 a needle assembly comprising cap 7, needle 6 and actuator 8 is clipped sealingly into position. The cap 7 keeps all the surfaces including the needle sterile after the assembly.

The assembly is preferably done in a clean room or aseptic conditions or environment or in an aseptic isolator or other sterile environment. The device components are either sterilised before filling by any suitable means such as ethylene oxide gas, radiation, steam autoclaving, dry heat or other method. The drug solution may be sterilised by any suitable method or any of the above methods or by aseptic filtration especially in the case of biopharmaceuticals.

FIGS. 22, 23, and 24 schematically illustrate the filling of an injector embodiment as described above in relation to FIGS. 4 and 5. The rigid container 1 of the injector defines a vent 91 that allows any gas trapped in the container 1 to escape during filling. A plug 92 may be placed in vent 91 to prevent any air entering after filling.

The rigid container or body may be made of a transparent material such as plastic or glass for visual inspection of the device.

Figure 25:
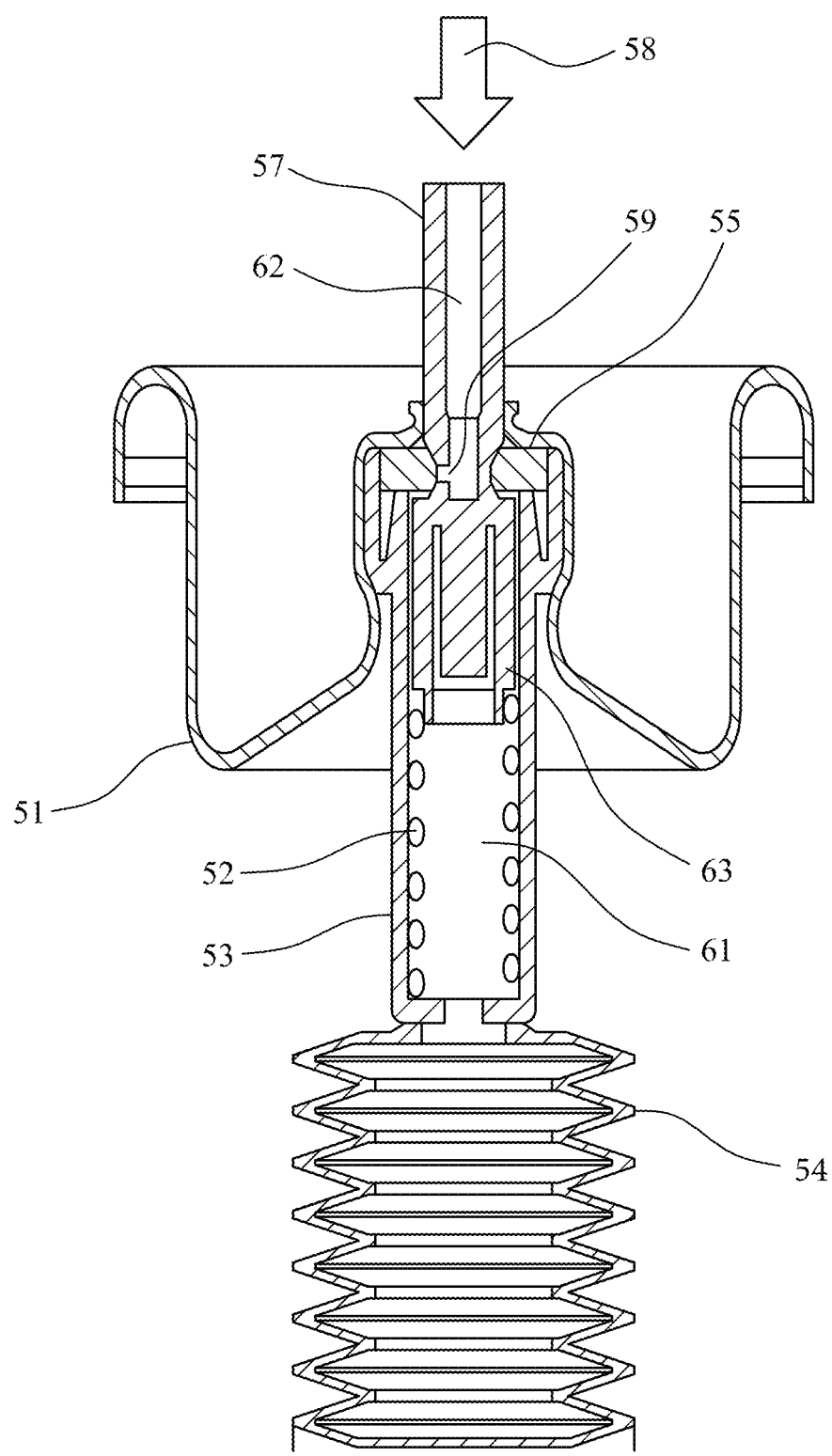

FIG. 25 illustrates a typical normally-closed valve which is suitable for use in an injector according to the invention. The valve is shown together with an attached bellows 54. FIG. 25 illustrates a male aerosol valve. It has a body 53 with a spring 52 within. A stem 57 has stem orifice 59 sealingly mounted against an inner gasket 55. A bellows 54 is sealingly connected to the valve body 53. When the stem 57 is depressed into the valve body 53 (the direction of arrow 58) the valve opens by exposing the stem orifice 59 to the pressurised liquid contents which are inside the valve cavities 61 and 63.

After filling the bellows 54 with drug contents via the valve, the valve stem 57 passageway 62 and stem orifice 59 (or gasket and cup in the case of a female valve) are preferably flushed with a clean liquid such as ethanol or any other suitable liquid or any suitable gas or a gas and liquid mixture or separately by both to ensure sterility.

It is preferable that the dead volumes 61, 62 and 63 in the valve are kept to a minimum.

The bellows 54 and valve body 53 may be moulded as one part in any suitable plastic material.

Figure 26:
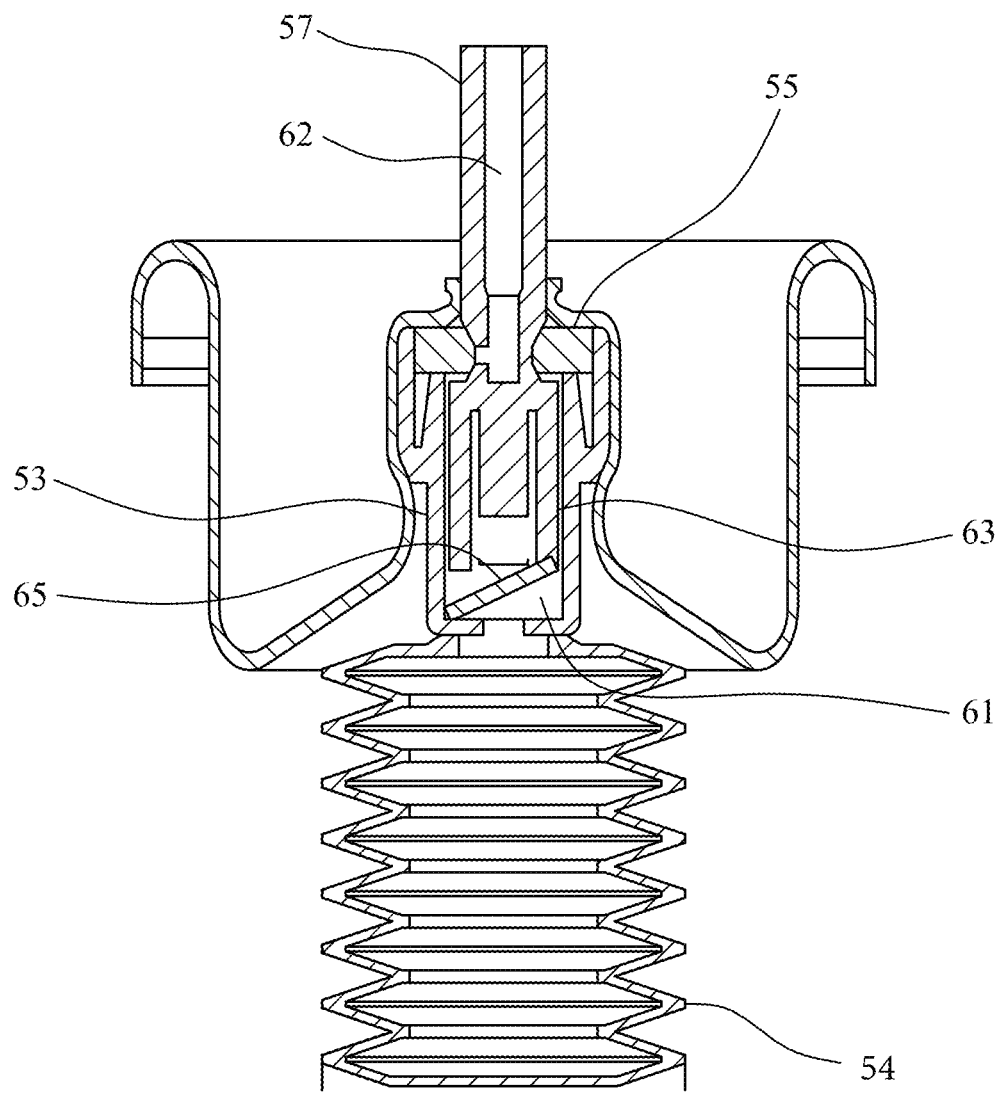

FIG. 26 illustrates a normally-closed valve in which the dead volume 61 is much reduced by eliminating the metal spring (spring 52 in FIG. 25). In FIG. 26 the valve comprises a spring 65 that is formed as part of the plastic stem 57. This eliminates the extra material of a separate spring and may help in minimising any drug stability issues. The valve shown in FIG. 26 can be manufactured from two materials. The stem 57 and spring 65, body 53 and bellows 54 can all be made from a single plastic. The only other material in contact with the drug solution is a gasket 55.

FIG. 27 illustrates a normally-closed valve in which a stem orifice 59 is located above an inner gasket 55 when the valve is closed and the stem passageway 62 is shortened to end at the point that the stem orifice 59 enters the stem 57. This may assist the flushing and cleaning of the stem after filling.

FIG. 28 illustrates a valve/bellows arrangement in which the bellows has concave bottom section 67. This configuration may help to minimise dead volume in the bellows when it is fully collapsed at the end of device use.

FIGS. 29 and 30 schematically illustrate an embodiment of an injector comprising a manual needle shield. The rigid container 1 forming the injector body has an outer case or cover 71, which locates and holds a shield 72 in position. A needle 6 is initially protected by a cap 9 prior to use as shown in FIG. 29. In FIG. 29 the shield 72 is shown in a pre-use position. In FIG. 30 it is shown in an activated position after being slid forward in direction of arrow 73 by the user.

A mechanical arrangement (not shown) locks the shield 72 in position so that the needle 6 is protected, thereby helping to prevent any needle stick injuries.

FIGS. 31 and 32 schematically illustrate an embodiment of an injector comprising an after use indicator. A window defined through the rigid container 1 allows a view of the bellows 2 within. After use, a marker 82 is visible through the window 81 indicating that the full dose has been injected. The injector is operated as normal by removing cap 9 and activating the injector by moving actuator 4 and needle 6 in direction of arrow 5.

FIGS. 33 and 34 schematically illustrate an embodiment of an injector comprising an alternative needle shield arrangement. An injector with a needle 6 has a protective cap 9, a hinged needle shield 92 hinged at a pivot point 93 and attached to container 1 by a strut 91. After removing the cap 9 and using the injector by emptying the bellows 2, the shield 92 is pivoted into its protective position covering needle 6 as shown by arrow 96.

FIGS. 35 and 36 schematically illustrate an embodiment of an injector having an alternative arrangement of an actuator to open the normally-closed valve. An actuator 4 is attached to a handle 101. To operate, after insertion of the needle into the body, a user places two fingers on finger pads 105 and another finger such as the thumb at a thumb contact point 106 on the rigid container 1 and presses as indicated by arrows 102 and 103. The container 1 is forced in the direction of arrow 103, depressing the actuator 8 and opening the normally-closed valve 4. Contents of the bellows 2 are forced out via needle 6 by spring 3.

FIG. 37 schematically illustrates an embodiment of an injector having an alternative arrangement of an actuator to open the normally-closed valve. The injector includes a casing defining two finger pads 105a and 105b. When inserting the needle 6 into a body, the finger pads 105b and thumb contact point 106 are pushed in the direction of arrows 102b and 103. To operate the injector, a user squeezes the finger pads 105a and point 106 on container 1 in the direction of arrows 102a and 103. This ensures a smooth and easy operation of the device as fingers can remain in the same place during needle insertion and injection.

FIGS. 38 and 39 schematically illustrate an embodiment of an injector in which an actuator 101 doubles as a needle shield. After use, the rigid container 1 is pulled back until spring loaded catch 111 engages to prevent the container 1, which carries the needle 6, being pushed out again, thereby making the device safe after use. Lugs 115 and 116 prevent the container 1 and needle 6 being completely separated from the actuator/shield 101.

FIGS. 40 and 41 schematically illustrate an embodiment of an injector in which an actuator 101 is spring loaded by means of a spring 112. The spring 112 is activated at the end of the injection by a release mechanism (not shown).

FIGS. 42 and 43 schematically illustrate an embodiment of an injector in which a piston or ram 121 is placed in between bellows 2 and spring 3 to transfer the spring's energy to the bellows 2. The piston or ram may ensure that the bellows 2 are pressurised evenly. The piston or ram may also act as an indicator, showing the level of liquid drug 10 contained within the bellows 2.

An injector as described herein may be used to inject any class of drug anywhere in the body of both humans and animals. Both conventional drugs and biopharmaceuticals may be used with the device. The injector may be filled with diluent for lyophilized drug reconstitution.

A cross-sectional view of an injector according to a preferred embodiment of the invention is illustrated in FIG. 44. The injector 1000 comprises a substantially cylindrical rigid container 1001 formed from transparent PET polymer. The rigid container 1001 defines a substantially cylindrical internal cavity 1101 which houses a transparent collapsible bellows 1002, a helical spring 1003, and a polymeric piston or ram 1121 located between the collapsible bellows 1002 and the helical spring 1003. The collapsible bellows 1002 is formed from polypropylene and is coupled to a normally-open aerosol valve 1004. The normally-open aerosol valve 1004 is crimped to an opening of the rigid container 1001, thereby sealing the contents of the rigid container.

A liquid medicament 1010 contained within the collapsible bellows 1002 is maintained under pressure by a force exerted on the collapsible bellows 1002 by the helical spring 1003 by means of the ram 1121. The ram 1121 is formed as an injection moulded polypropylene component and acts as a guide to the force exerted by the spring 1003. The ram helps to ensure that the pressure from the spring is applied evenly to the collapsible bellows.

A hypodermic needle 1006 is coupled to the aerosol valve 1004 by way of an actuating element 1008 which acts to open the normally-closed aerosol valve 1004 when the actuator 1008 is depressed. A cap 1009 shields the hypodermic needle 1006.

An upper surface of the ram 1121 is bevelled or formed into a substantially conical shape 1122. Furthermore, an insert 1130 is disposed within the chamber 1101 of the rigid container 1001 between the collapsible bellows 1002 and the aerosol valve 1004. This insert 1130 has a bevelled surface that substantially matches the bevelled surface of the ram 1121.

FIGS. 45 to 47 illustrate the steps taken to manufacture an injector according to the embodiment illustrated in FIG. 44.

FIG. 45 illustrates the steps required to manufacture a bellows/valve sub-assembly 1300. A bellows is physically connected to an aerosol valve 1004 with an insert 1130 disposed in between. This coupling may be by a suitable means such as by welding or by adhesive connection.

FIG. 46 illustrates the components required to assemble a container sub-assembly 1400. The container sub-assembly is formed from the transparent rigid container 1001, the helical spring 1003 and the ram 1121. The helical spring is placed within the rigid container 1001 and the ram 1121 slides over an upper surface of the helical spring.

The components forming the valve/bellows sub-assembly and the container sub-assembly are sterilised, for example by gamma irradiation.

On assembly, any air within the rigid container cavity 1101 is removed and replaced with an inert atmosphere of nitrogen. This is achieved by known "under the cup" vacuuming techniques.

The valve/bellows sub-assembly is inserted into the container sub-assembly and the valve is crimped to attach the valve/bellows sub-assembly to the rigid container sub-assembly and to seal the rigid container.

The collapsible bellows 1002 is filled with a liquid drug, or with a mixture of soluble powdered drug and a suitable solvent such as water for injection such that a liquid drug is formed, and then the normally-closed valve is closed to retain the liquid within the collapsible bellows. The act of inserting the liquid into the collapsible bellows causes the helical spring 1003 to compress. Thus, the liquid within the collapsible bellows is under pressure and will be released from the device when the aerosol valve is opened.

FIG. 47 illustrates the coupling of the hypodermic needle to the aerosol valve.

It is preferred that the injector comprises an ergonomic outer casing. Thus, the injector 1000 may be further encased by an outer casing 1500, a needle shield/actuator 1550 and a removable cap 1600.

The outer casing 1500 includes a transparent window 1510 through which the ram 1121 and the helical spring 1003 of the injector 1000 may be seen.

The needle shield/actuator 1550 acts to shield the hypodermic needle 1006 until it is actually used, and simultaneously acts to depress the actuator 1008 when the needle has been inserted to a predetermined depth. The cap 1600 maintains cleanliness and sterility of the device until use. The result of the encasement of the injector 1000 is an encased injector 2000 that is ready for shipment to a user.

FIG. 49 illustrates the steps involved in using the encased injector 2000.

In step A the user removes the cap 1600, thereby exposing the needle shield/actuator. The encased injector 2000 is then pressed into the user as illustrated in step C. The needle shield is depressed and the needle extends beyond the needle shield, thereby piercing the patient's skin. When the needle has reached a predetermined depth the valve 1004 is opened, thereby automatically releasing the liquid medicament contained within the injector into the patient.

The invention claimed is:

1. An injector for delivering a liquid medicament comprising:
    a collapsible container for containing the liquid medicament, a normally-closed valve coupled to the collapsible container for retaining the liquid medicament within the collapsible container;
    an injection means coupled to the normally-closed valve for delivering the liquid medicament from the collapsible container;
    pressurising means for maintaining the liquid medicament contained within the collapsible container under pressure during storage before actuation of the injector, such that the liquid medicament is delivered by the injection means when the normally-closed valve is opened; and
    an actuator for opening the normally-closed valve, in which the normally-closed valve opens in response to the actuator being pressed against a patient's skin;
    wherein, when the normally-closed valve is opened, the liquid medicament is delivered by the injection means due to the pressure from the pressurising means.

2. An injector according to claim 1 in which the injection means is a hollow needle, the hollow needle being a hypodermic needle.

3. An injector according to claim 1 in which the collapsible container and the pressurising means are housed within a rigid container.

4. An injector according to claim 3 in which at least a portion of the rigid container is transparent.

5. An injector according to claim 3 in which the rigid container includes a vent to allow displaced air within the rigid container to escape when the collapsible container is filled.

6. An injector according to claim 3 in which the rigid container is hermetically sealed.

7. An injector according to claim 6 in which the rigid container has an inert gas atmosphere surrounding the collapsible container.

8. The injector according to claim 3 wherein the normally-closed valve is connected to the rigid container.

9. The injector according to claim 4 wherein the rigid container is formed from a transparent polymer or glass.

10. The injector according to claim 5 wherein the vent is a closable vent.

11. The injector according to claim 7 wherein the inert gas has a low solubility in the liquid medicament.

12. The injector according to claim 11 wherein the inert gas is nitrogen.

13. An injector according to claim 1 in which the collapsible container is defined by internal walls of the rigid container and a piston that is slidably arranged within the rigid container, the volume of the collapsible container varying depending on the position of the piston.

14. An injector according to claim 1 in which the collapsible container is a bellows coupled to the normally-closed valve.

15. An injector according to claim 14 in which the bellows is formed from a transparent material.

16. An injector according to claim 1 in which the pressurising means is a biasing element that exerts a force that acts on the collapsible container.

17. An injector according to claim 16 in which the force acting to collapse the collapsible container is generated by a spring.

18. An injector according to claim 17 in which the pressurising means comprises a spring and is an integral part of the collapsible container.

19. The injector according to claim 17 wherein the spring is a helical spring arranged to urge the collapsible container to collapse.

20. The injector according to claim 17 wherein the spring comprises a plastic spring.

21. An injector according to claim 16 in which the force that acts on the collapsible container is generated by a compressed gas or a liquefied gas.

22. An injector according to claim 16 in which the pressurising means comprises a piston or ram that is urged by the force into contact with the collapsible container.

23. An injector according to claim 1 in which the normally-closed valve is a continuous flow valve or an aerosol valve.

24. An injector according to claim 1 in which the normally-closed valve comprises a spring that acts to urge the valve to a closed position, in which the spring is a non-metallic spring.

25. An injector according to claim 1 in which the injection means is a needle and the normally-closed valve is arranged to open when the needle has been inserted a predetermined distance into the patient, the predetermined distance depending on the type of drug that is being delivered and the tissue that the delivery is required to be made into.

26. An injector according to claim 1 in which the injector means is a needle and the injector comprises a protective sleeve or shield.

27. An injector according to claim 1 when filled with the liquid medicament.

28. An injector comprising:
    a collapsible container retaining a liquid medicament by a normally-closed valve; and
    a needle for injecting the liquid medicament coupled to the normally-closed valve;
    a force arranged for maintaining the liquid medicament retained within the collapsible container under pressure during storage before actuation of the injector, such that the liquid medicament is delivered through the needle when the normally-closed valve is opened; and
    an actuator for opening the normally-closed valve, in which the normally-closed valve opens in response to the actuator being pressed against a patient's skin;
    wherein, when the normally-closed valve is opened, the liquid medicament is delivered by the needle due to the pressure from the force.

29. An injector according to claim 28 in which at least an inner surface of the collapsible container is formed from a polymer and the normally-closed valve is formed from a polymer such that the liquid medicament is does not come into contact with any metallic component while retained within the collapsible container.

30. An injector according to claim 28 in which the liquid medicament does not contact the needle until the normally-closed valve is opened to deliver the liquid medicament.

31. An injector according to claim 28 in which the liquid medicament comprises a constituent classified within one of the following categories of pharmaceuticals or biopharmaceuticals: Alpha1-Adrenergic Antagonists, Analgesic Agents, Anaesthetics, Angiotensin Antagonists, Anti-Inflammatory Agents, Antianxiety Agents, Antiarrhythmics, Anticholinergics, Anticoagulants, Anticonvulsants, Antidiarrheal Agents, Antihistamines, Antineoplastics and Antimetabolites, Antineoplastics and Antimetabolites, Antiplasticity Agents, Antiulcer Agents, Beta-Adrenergic Antagonists, Bisphosphonates, Bronchodilators, Cardiac Inotropes, Cardiovascular Agents, Central Acting Alpha2-stimulants, Contrast Agents, Converting Enzyme Inhibitors, Dermatologies, Diuretics, Drugs for Erectile Dysfunction, Drugs of Abuse, Endothelin Antegonists, Hormonal Agents and Cytokines, Hypoglycemic Agents, Hypouricemic Agents and Drugs Used For Gout, Immunosuppressants, Lipid Lowering Agents, Miscellaneous, Psychotherapeutic Agents, Renin Inhibitors, Serotonergic Antagonist, Steroids, Sympathomimetics, Thyroid and Antithyroid Agents, Vasodilators, Vasopeptidase Inhibitors, Salines, Insulins, Blood factors, Thrombolytic agents, Hormones, Haematopoietic growth factors, Interferons, Interleukin-based products, Vaccines, Monoclonal antibodies, Tumour necrosis factors, Therapeutic enzymes, Antibody-drug conjugates, Biosimilars, Erythropoietin, Immunoglobulin, Blood and Blood components, Allergenics, Somatic cells, Gene therapy, Tissues, and Recombinant therapeutic proteins.

32. An injector according to claim 28 that is a hand-held injector.

33. An injector according to claim 28 in which the dead volume of the collapsible container and the normally-closed valve are low enough to ensure that more than 85% of the liquid medicament contained within the collapsible container can be delivered.

34. The injector according to claim 33 wherein more than 90% of the liquid medicament contained within the collapsible container can be delivered.

35. The injector according to claim 33 wherein more than 95% of the liquid medicament contained within the collapsible container can be delivered.

36. The injector according to claim 33 wherein more than 97% of the liquid medicament contained within the collapsible container can be delivered.

37. A method of injecting a liquid medicament, the liquid medicament being retained within a collapsible container of an injector by a normally-closed valve, the injector comprising an actuator for opening the normally-closed valve and a needle coupled to the normally-closed valve and used for injecting the liquid medicament, the actuator when pressed against a patient's skin opening the normally-closed valve, the method comprising the steps of:

positioning the needle of the injector to deliver the liquid medicament to a patient, whereby a force is arranged for maintaining the liquid medicament under pressure during storage before actuation of the injector, such that the liquid medicament is delivered through the needle when the normally-closed valve is opened; and pressing the actuator against skin of the patient, from which the normally-closed valve opens, whereby the liquid medicament is injected due to the pressure from the force.

38. A method according to claim 37 in which the normally-closed valve is opened automatically when the injector is positioned correctly for delivery.

39. A method according to claim 38 in which the normally-closed valve is actuated when the needle is inserted into the patient to a predetermined depth.

40. A method of manufacturing an injector for delivering a liquid medicament comprising the steps of:

coupling a normally-closed valve to a collapsible container for containing the liquid medicament;

opening the normally-closed valve;

filling the collapsible container with the liquid medicament through the normally-closed valve, thereby causing the collapsible container to expand and deflect a pressurising means;

closing the normally-closed valve to retain the liquid medicament within the collapsible-container, the liquid medicament within the collapsible container being maintained under pressure during storage before actuation of the injector due to the pressurising means; and coupling the normally-closed valve to an injection means for delivering the liquid medicament from the collapsible container when the normally-closed valve is opened;

wherein the injection means comprises an actuator for opening the normally-closed valve, the actuator when pressed against a patient's skin opens the normally-closed valve, and when the normally-closed valve is opened, the liquid medicament is delivered by the injection means due to the pressure from the pressurising means.

41. A method according to claim 40 further comprising the step of applying a vacuum to the collapsible-container through the normally-closed valve to remove air trapped within the collapsible container and the normally-closed valve prior to filling.

42. A method according to claim 40 in which the normally-closed valve is flushed with a sterilising fluid, prior to coupling to the injection means.

43. The method according to claim 42 wherein the sterilizing fluid comprises ethanol.

44. A method according to any of claim 40 in which air is evacuated from the rigid container.

45. The method according to claim 44 wherein the air is replaced by an inert gas.

* * * * *